United States Patent
Bang et al.

(10) Patent No.: US 7,625,926 B2
(45) Date of Patent: Dec. 1, 2009

(54) P-GLYCOPROTEIN INHIBITOR, METHOD FOR PREPARING THE SAME AND PHARMACEUTICAL COMPOSITION COMPRISING THE SAME

(75) Inventors: Keuk Chan Bang, Incheon (KR); Mi Young Cha, Seongnam-si (KR); Young Gil Ahn, Seongnam-si (KR); Young Jin Ham, Seoul (KR); Maeng Sup Kim, Seoul (KR); Gwan Sun Lee, Seoul (KR)

(73) Assignee: Hanmi Pharm. Co., Ltd, Hwaseong-gun (KR)

( * ) Notice: Subject to any disclaimer, the term of this patent is extended or adjusted under 35 U.S.C. 154(b) by 534 days.

(21) Appl. No.: 10/574,098

(22) PCT Filed: Oct. 6, 2004

(86) PCT No.: PCT/KR2004/002550

§ 371 (c)(1),
(2), (4) Date: Mar. 31, 2006

(87) PCT Pub. No.: WO2005/033097

PCT Pub. Date: Apr. 14, 2005

(65) Prior Publication Data

US 2007/0072900 A1    Mar. 29, 2007

(30) Foreign Application Priority Data

Oct. 7, 2003  (KR) ............... 10-2003-0069582

(51) Int. Cl.
*C07D 401/14* (2006.01)
*A61K 31/4709* (2006.01)

(52) U.S. Cl. .............. 514/307; 514/381; 546/148; 548/253

(58) Field of Classification Search .............. None
See application file for complete search history.

(56) References Cited

FOREIGN PATENT DOCUMENTS

| JP | 5-43544 A2 | 2/1993 |
|---|---|---|
| KR | 10-580743 B1 | 5/2006 |
| WO | WO 92/7844 A1 | 5/1992 |
| WO | WO 94/01408 A1 | 1/1994 |
| WO | WO 98/17648 A1 | 4/1998 |
| WO | WO 03/095447 A1 | 11/2003 |

OTHER PUBLICATIONS

M. Roe et al., "Reversal of P-Glycoprotein Media Multidrug Resistance by Novel Anthranilamide Derivatives", Bioorganic & Medicinal Chemistry Letters 9, (4), 1999, pp. 595-600.

P. Mistry et al., "In Vitro *and* in Vivo Reversal of P-Glycoprotein-mediated Multidrug Resistance by a Novel Potent Modulator, XR9576", Cancer Research, 61 (2), Jan. 15, 2001.

A. Stewart et al., "Phase I Trial of XR9576 in Healthy Volunteers Demonstrates Modulation of P-Glycoprotein in CD56+Lymphocytes after Oral and Intravenous Administration", Clinical Cancer Research, vol. 6, Nov. 2000, pp. 4186-4191.

W. Shouming et al., "Studies on Quinazolinones as Dual Inhibitors of Pgp and MRP1 in Multidrug Resistance", Bioorganic & Medicinal Chemistry Letters, 2002, vol. 12, No. 4, pp. 571-574.

M.N. Borrel et al., "Mobile ionophores are a novel class of P-glycoprotein inhibitors. The effects of ionophores on 4'-O-tetrahydropyranyladriamycin incorporation in K562 drug-resistant cells", European Journal of Biochemistry, 1994, vol. 233, No. 1, pp. 125-133.

W.N. Hait et al., "Rational design and preclinical pharmacology of drugs for reversing multidrug resistance", Biochemical Pharmacology, 1992, vol. 43, No. 1, pp. 103-107.

*Primary Examiner*—Zinna N Davis
(74) *Attorney, Agent, or Firm*—Sughrue Mion, PLLC

(57) ABSTRACT

The bioavailability of an anticancer agent is enhanced when the anticancer agent is administered together with a pharmaceutical composition comprising a compound of formula (I) or a pharmaceutically acceptable salt thereof.

9 Claims, No Drawings

P-GLYCOPROTEIN INHIBITOR, METHOD FOR PREPARING THE SAME AND PHARMACEUTICAL COMPOSITION COMPRISING THE SAME

This is a national stage application under 35 U.S.C. §371 of PCT/KR2004/002550 filed on Oct. 6, 2004, which claims priority from Korean patent application 10-2003-0069582 filed on Oct. 7, 2003, all of which are incorporated herein by reference.

FIELD OF THE INVENTION

The present invention relates to an effective p-glycoprotein inhibitor and a pharmaceutically acceptable salt thereof, a method for preparing the same and a pharmaceutical composition containing the same as an active ingredient.

BACKGROUND OF THE INVENTION

It is known that many anticancer agents, e.g., vinca alkaloid, anthracycline, epipodophilotoxin, paclitaxel and docetaxel, become in effective when administered to a patient having multi-drug resistance (MDR) which has been caused by the presence of overexpressed p-glycoprotein in the patent. P-glycoprotein inhibits intracellular accumulation of the administered anticancer agent by pumping the agent out of the cell (D. W. Shen, et al., Science (1986), 232, 643-645; and Schinkel, et al., Cell (1994), 77, 491-502). Accordingly, there have been numerous attempts to enhance the bioavailability of the above-mentioned agents by incorporating therein an inhibitor of p-glycoprotein.

Since the conventional p-glycoprotein inhibitors, such as verapamil and cyclosporin A, cause serious adverse effects, e.g., blood pressure decline and immunity suppression, a number of new p-glycoprotein inhibitors such as piperidine-2-carboxylate, acridine, piperazine-2,5-dion, anthranilic acid and methanodibenzosuberan derivatives have been developed. However, such newly introduced p-glycoprotein inhibitors have been reported to have toxicity and other problems (see PCT Publication No. WO 94/07858; WO 92/12132; WO 96/20180 and 98/17648; and WO 98/22112).

Accordingly, the present inventors have endeavored to develop a p-glycoprotein inhibitor that is free from the above problems, and have found a novel compound which markedly enhances the bioavailability of anticancer agents by suppressing p-glycoprotein.

SUMMARY OF THE INVENTION

Accordingly, it is an object of the present invention to provide a compound which can be used as an effective p-glycoprotein inhibitor for enhancing the bioavailability of an anticancer agent while minimizing adverse effects.

It is another object of the present invention to provide a process for preparing such compound.

It is a further object of the present invention to provide a pharmaceutical composition containing such compound.

DETAILED DESCRIPTION OF THE INVENTION

In accordance with one aspect of the present invention, there is provided a compound of formula (I) and a pharmaceutically acceptable salt thereof:

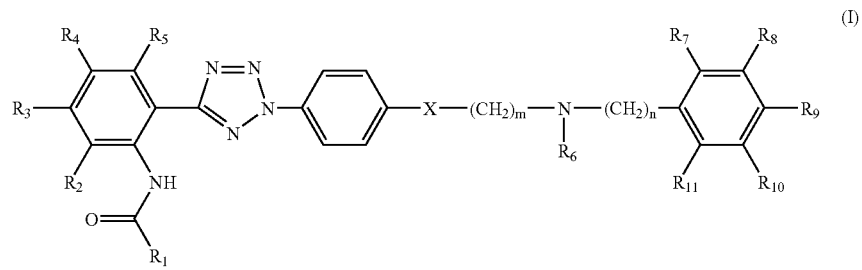

wherein, $R_1$ is aryl, heteroaryl, acrylaryl, acrylheteroaryl, heterocycloalkenyl, or carbocyclo, which is optionally substituted with one or more substituents selected from $C_{1-5}$ alkyl, hydroxy, $C_{1-5}$ alkoxy, halogen, trifluoromethyl, nitro and amino;

$R_2$, $R_3$, $R_4$, $R_5$, $R_6$, $R_7$, $R_8$, $R_9$, $R_{10}$ and $R_{11}$ are each independently hydrogen, hydroxy, halogen, nitro, $C_{1-5}$ alkyl or alkoxy, $R_6$ and $R_{11}$ being optionally fused together to form a 4 to 8-membered ring;

m and n are each independently an integer ranging from 0 to 4; and

X is $CH_2$, O or S.

Unlike the conventional p-glycoprotein inhibitors, e.g., cyclosporin A, cinchonine and verapamil, the compound of formula (I) itself has no pharmacological activity, and, consequently, causes no side effects, while enhancing the bioavailability of anticancer agents by inhibiting the activity of p-glycoprotein.

In the compound of formula (I) of the present invention, preferred $R_1$ is unsubstituted or substituted phenyl, pyridine, pyrazine, quinoline, isoquinoline, quinazoline, quinoxaline, pyrazole, imidazole, triazole, oxazole, thiazole, oxadiazole, thiadiazole, benzthiazole, benzoxazole, chromone, quinolone, cinnamic or quinoline acryl.

Representative examples of the compound of formula (I) include:

quinoline-3-carboxylic acid [2-(2-4-[2-(6,7-dimethoxy-3,4-dihydro-1H-isoquinolin-2-yl)-ethyl]-phenyl-2H-tetrazol-5-yl)-4,5-dimethoxy-phenyl]-amide;

quinoline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

isoquinoline-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

quinoline-8-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

isoquinoline-1-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

quinoline-4-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

4-methoxy-quinoline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

quinoxaline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

pyridine-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-nicotinamide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-isonicotinamide;

pyrazine-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-benzamide;

naphthalene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-2-fluoro-benzamide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-fluoro-benzamide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-4-fluoro-benzamide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3,4-difluoro-benzamide;

thiophene-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

furan-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

6-methyl-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

5-hydroxy-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

5-methoxy-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

6-fluoro-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

6-bromo-4-oxo-4H-chromene-2-carboxylic acid [2-(2-{4-[2-(6,7-dimethoxy-3,4-dihydro-1H-iso quinolin-2-yl)-ethyl]-phenyl}-2H-tetrazol-5-yl)-4,5-dimethoxy-phenyl]-amide;

cinoline-4-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

4-oxo-4H-chromene-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

quinoline-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-difluoro-phenyl]-amide;

quinoline-3-carboxylic acid [2-(2-{4-[2-(6,7-dimethoxy-3,4-dihydro-1H-isoquinolin-2-yl)-ethylsulfanyl]-phenyl}-2H-tetrazol-5-yl)-4,5-dimethoxy-phenyl]-amide;

N-(2-(2-(4-(2-(6,7-dimethoxy-3,4-dihydroisoquinolin-2 (1H)-yl)-ethyl)phenyl)-2H-tetrazol-5-yl)-4,5-dimethoxy-phenyl)quinoline-3-carboxamide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-phenyl-acrylamide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-quinolin-1-yl-acrylamide; and 4-oxo-4H-chromene-2-carboxylic acid (2-{2-[4-(2-{[2-(3,4-dimethoxy-phenyl)-ethyl]-methyl-amino}-ethyl)-phenyl]-2H-tetrazol-5-yl}-4,5-dimethoxy-phenyl)-amide.

The compound of formula (I) may be prepared by the following Reaction Scheme A:

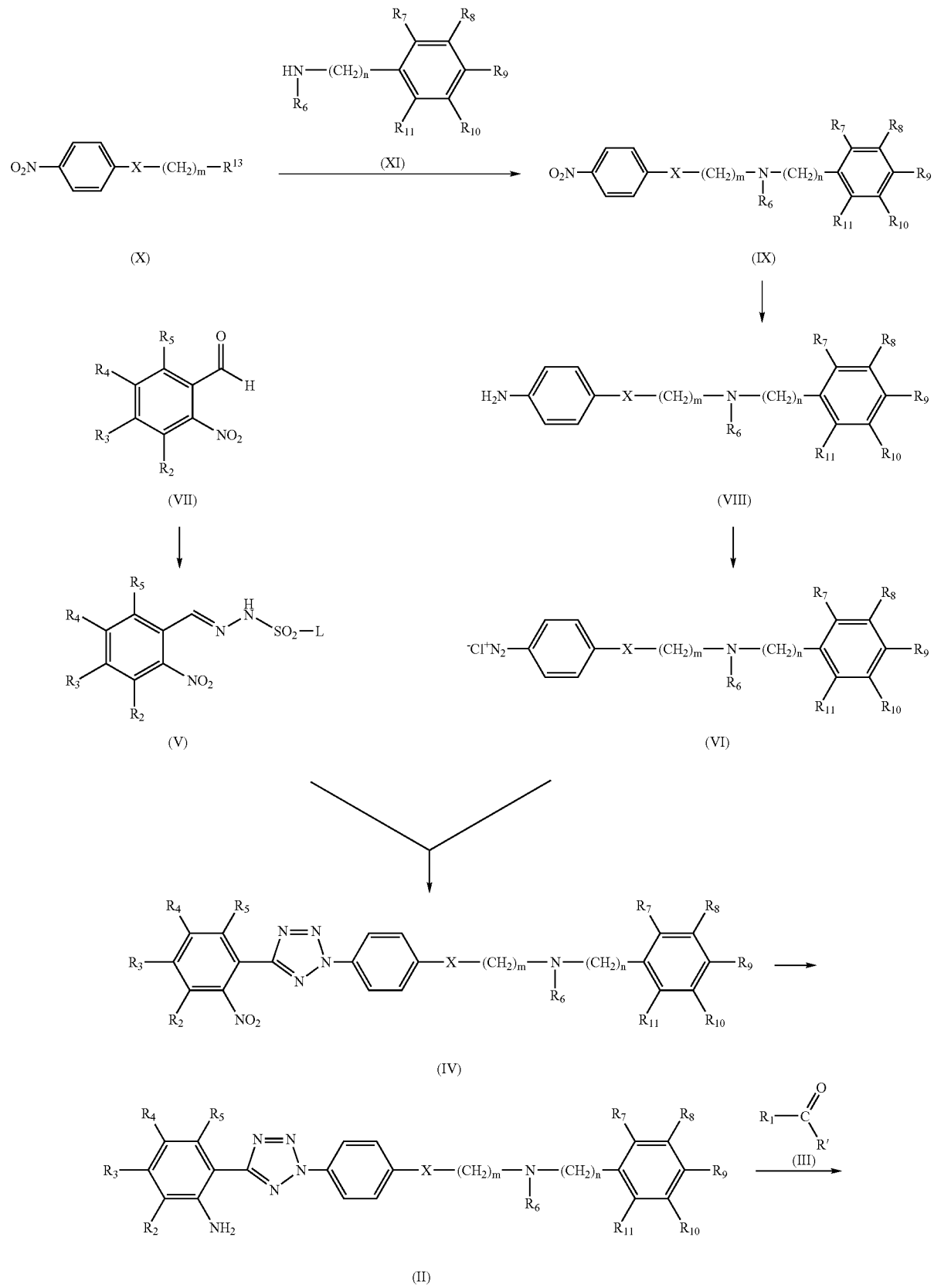

-continued

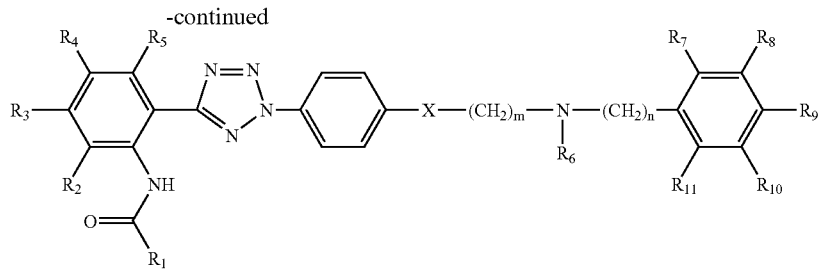

(I)

wherein:

$R_1, R_2, R_3, R_4, R_5, R_6, R_7, R_8, R_9, R_{10}, R_{11}$ m, n and X have the same meanings as defined in formula (I);

R' and R'' are each dependently OH, Cl or Br, and

L is benzyl or tolyl.

In Reaction Scheme A, the compound of formula (I) may be prepared by (i) cyclizing a compound of formula (V) with a compound of formula (VI) in the presence of a base to obtain a compound of formula (IV); (ii) hydrogenating the compound of formula (V) in the presence of a catalyst to obtain a compound of formula (II); and (iii) acylating the compound of formula (II) obtained in step (ii) with a compound of formula (m) in the presence of a base or a condensing agent.

The base used in step (i) may be selected from the group consisting of pyridine, triethylamine and diisopropylethylamine. Step (i) may be conducted in a solvent such as methanol, ethanol, chloroform, dichloromethane, tetrahydrofuran, ethylether, hexane and toluene, and the compound of formula (VI) may be employed in an amount ranging from 1 to 2 equivalents based on 1 equivalent of the compound of formula (V).

Step (ii) may be conducted in a solvent, such as methanol, ethanol, chloroform, dichloromethane, tetrahydrofuran, ethylether, hexane and toluene, at a temperature ranging from 0 to 50° C.; and the catalyst for step (ii) may be selected from the group consisting of palladium, platinum and zinc catalysts.

In step (iii), the compound of formula (III) may be employed in an amount ranging from 1 to 1.5 equivalents relative to 1 equivalent of the compound of formula (II). The base of step (iii) may be used in an amount ranging from 1 to 2 equivalents per 1 equivalent of the compound of formula (II), while the condensing agent may be present in an amount ranging from 1 to 5 equivalents, preferably from 1 to 2 equivalents per 1 equivalent of the compound of formula (II). The base for step (iii) encompasses triethylamine, dipropylethylamine and pyridine; and the condensing agent in step (iii) may be selected from the group consisting of 1-(3-dimethylaminopropyl)-3-ethylcarbodiimide, N,N'-dicyclohexylcarbodiimide, N,N'-diisopropylcarbodiimide and 1-cyclohexyl-3-(2-(morpholinoethyl)carbodiimide)methyl-p-toluenesulfonate, preferably 1-(3-dimethylaminopropyl)-3-ethylcarbodiimide. In case the condensing agent is used in step (iii), 4-(dimethylamino)pyridine may be added as a catalyst in an amount ranging from 0.05 to 0.3 equivalent based on 1 equivalent of the compound of formula (II). The acylation of the compound of formula (II) may be carried out in a solvent selected from the group consisting of dichloromethane, chloroform, N,N-dimethylformamide, tetrahydrofuran and 1,4-dioxane, preferably dichloromethane and chloroform, at a temperature ranging from −20° C. to the boiling point of the solvent employed, preferably from 10 to 40° C.

In Reaction Scheme A, the compound of formula (V) may be prepared by reacting a compound of formula (VII) with toluenesulfonyl chloride or benzenesulfonyl chloride according to the method described in Bulletin of the Chemical Society of Japan Vol. 49(7), 1920-1923 (1976). In this reaction, toluenesulfonyl chloride or benzenesulfonyl chloride may be used in an amount ranging from 0.5 to 5 equivalents, preferably from 1 to 2 equivalents, per 1 equivalent of the compound of formula (VII), and the reaction may be conducted in a solvent selected from the group consisting of chloroform, tetrahydrofuran, ethanol, methanol and water, at a temperature ranging from −10 to 20° C., preferably from 0 to 5° C.

Also, the compound of formula (VI) may be prepared by reacting a compound of formula (X) with a compound of formula (XI) in the presence of a base, e.g., pyridine, triethylamine or diisopropylethylamine, to obtain a compound of formula (IX), hydrogenating the compound of formula (IX) in the presence of a catalyst to form a compound of formula (VIII), and reacting the compound of formula (VIII) with sodium nitrite and HCl (see Bulletin of the Chemical Society of Japan Vol. 49(7), 1920-1923 (1976)).

In this preparation, the reaction between the compound of formula (X) and the compound of formula (XI) may be carried out in a solvent selected from the group consisting of methanol, ethanol, chloroform, dichloromethane, tetrahydrofuran, ethylether, hexane and toluene, at a temperature ranging from 0 to 50° C.

The catalyst suitable for this preparation is a metallic catalyst such as palladium, platinum or zinc catalyst, and the hydrogenation of the compound of formula (IX) may be conducted in a solvent such as methanol, ethanol, chloroform, dichloromethane, tetrahydrofuran, ethylether, hexane or toluene, at a temperature ranging from 0 to 50° C.

The amount of sodium nitrite used in this preparation may range from 1 to 5 equivalents, preferably from 1 to 3 equivalents, per 1 equivalent of the compound of formula (VIII), while HCl may be employed in an amount ranging from 0.5 to 1 equivalent based on 1 equivalent of the compound of formula (VIII). The reaction converting the compound of formula (VII) into the compound of formula (VI) may be conducted in a solvent such as ethanol, methanol or water, at a temperature ranging from −10 to 20° C., preferably from 0 to 5° C.

Furthermore, the present invention encompasses, within its scope, a pharmaceutically acceptable salt of the p-glycoprotein inhibitor of formula (I) derived with an inorganic or organic acid. A preferred inorganic or organic acid may be selected from the group consisting of hydrochloric acid, hydrobromic acid, sulfuric acid, phosphoric acid, nitric acid, acetic acid, glycolic acid, lactic acid, pyrubic acid, malonic acid, succinic acid, glutamic acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The p-glycoprotein inhibitor of the present invention may be administered in combination with an anticancer agent which is not readily absorbed in the digestive tract due to the inhibitory action of p-glycoprotein. Thus, in a further aspect, the present invention provides a composition comprising the p-glycoprotein inhibitor of formula (I) or a pharmaceutically acceptable salt thereof together with an anticancer agent, which is effective in:

(a) improving or increasing the efficacy of the anticancer agent;

(b) increasing or restoring the susceptibility of a tumor to the anticancer agent; or (c) reducing or reversing MDR of a tumor to the anticancer agent regardless of whether the MDR is acquired, induced or innate.

Preferred examples of the anticancer agent include taxan (e.g., paclitaxel and docetaxel), vinca alkaloid (e.g., vincristine, vinblastine and vinorelbine), anthracycline (e.g., daunomycin, daunorubicin, doxorubicin and aclarubicin), camptothecin (e.g., topotecan and irinotecan), podophyllotoxin (e.g., etoposide and VP16), mitoxantrone, actinomycin, colchicine, gramicidine D, and amsacrine.

In a further aspect, the present invention provides a pharmaceutical composition comprising the compound of formula (I) or a pharmaceutically acceptable salt thereof as an effective ingredient together with pharmaceutically acceptable carriers, expients, or other additives, for the treatment of a mammal which suffers from a cancer:

(a) to improve or increase the efficacy of an anticancer agent;

(b) to increase or restore the susceptibility of a tumor to the anticancer agent; or (c) to reduce or reverse MDR of a tumor to the anticancer agent regardless of whether the MDR is acquired, induced or innate.

The pharmaceutical composition of the present invention may be formulated for oral administration, or parenteral administration such as intramuscular, intravenous or transdermal administration.

For oral administration, the pharmaceutical composition of the present invention may take the form of tablet, coated tablet, powder, rigid or soft gelatin capsule, solution, emulsion, microemulsion, or aqueous dispersion prepared in the conventional manner together with at least one pharmaceutically acceptable excipients, such as binding agents (e.g., pregelatinized maize starch, polyvinylpyrrolidone and hydroxypropyl methylcellulose); fillers (e.g., lactose, microcrystalline cellulose and calcium hydrogen phosphate); lubricants (e.g., magnesium stearate, talc and silica); disintegrants (e.g., sodium lauryl sulphate and sodium starch glycolate). These tablets may be coated by the methods well known in the art. Liquid preparations for oral administration may take the form of, for example, solutions, syrups or suspensions, or they may be presented as a dry product for constitution with water or other suitable vehicle before use. Such liquid preparations may be prepared by the conventional means together with at least one pharmaceutically acceptable additive such as a suspending agent (e.g., sorbitol syrup, a cellulose derivative and a hydrogenated edible fat); an emulsifying agent (e.g., lecithin and acacia); a non-aqueous vehicle (e.g., almond oil, oily ester, ethyl alcohol and fractionated vegetable oil); and a preservative (e.g., methyl or propyl-p-hydroxybenzoate and sorbic acid). These preparations may also contain at least one buffer salt or at least one flavouring, colouring or sweetening agent as appropriate.

The pharmaceutical composition of the present invention may be formulated for parenteral administration by bolus injection or continuous infusion. Formulations for injection may be presented in unit dosage form e.g., in ampoules or in multi-dose containers, with an added preservative. The pharmaceutical compositions may take the form of suspensions, solutions or emulsions in oily, aqueous or alcoholic vehicles, and contain surfactants, suspensions or emulsifiers, which may be selected from water, saline solution, glucose solution, sugar-like solution, alcohol, glycol, ether (e.g. polyethyleneglycol 400), oil, fatty acid, fatty acid ester and glyceride.

The pharmaceutical composition of the present invention may be administered alone, before or after the administration of an anticancer agent, or in combination with the anticancer agent.

A proposed daily dose of the compound of the present invention for administration to a human (of approximately 70 kg body weight) is about from 0.1 mg/kg to 100 mg/kg, more preferably about from 1 mg/kg to 20 mg/kg. It should be understood that the daily dose should be determined in light of various relevant factors including the condition to be treated, the severity of the patient's symptoms, the route of administration, or the physiological form of the anticancer agent; and, therefore, the dosage suggested above should not be construed to limit the scope of the invention in anyway.

The following Examples are intended to further illustrate the present invention without limiting its scope.

Example 1

Synthesis of quinoline-3-carboxylic acid [2-(2-4-[2-(6,7-dimethoxy-3,4-dihydro-1H-isoquinolin-2-yl)-ethyl]-phenyl-2H-tetrazol-5-yl)-4,5-dimethoxy-phenyl]-amide Step 1: Preparation of 4-[2-(6,7-dimethoxy-3,4-dihydro-1H-isoquinolin-2-yl)-ethyl]-phenylamine 2.30 g of 2-(4-nitrophenyl)ethane bromide and 2.29 g of 6,7-dimethoxy-1,2,3,4-tetrahydroisoquinoline hydrochloride were dissolved in 150 ml of N,N'-dimethylformamide, 4.15 g of potassium carbonate and 1.80 g of sodium iodide were added thereto, and the mixture was allowed to react at 100° C. for 12 hours. After mixing 150 ml of water, the reaction mixture was extracted three times with 200 ml portion of ethylacetate, and the combined organic layer was washed with saturated NaCl and dried over magnesium sulfate. The resulting solution was subjected to a reduced pressure to remove the solvent, and the residue was recrystallized using ethylacetate, to obtain 2.40 g of a nitro derivative. The nitro derivative was added to a mixture of 150 ml of tetrahydrofuran and 150 ml of methanol, 0.24 g of Pd/C was added thereto, and reduced under an atmospheric hydrogen pressure for 18 hours. The resulting solution was filtrated and concentrated under a reduced pressure to obtain a residue that gave 2.03 g of the title compound (yield 65%).

$^1$H-NMR(CDCl$_3$) δ: 6.97 (d, 2H), 6.57 (d, 2H), 6.53 (s, 1H), 6.47 (s, 1H), 3.77 (s, 6H), 3.57 (s, 2H), 3.50 (s, 2H), 2.71 (m, 8H)

Step 2: Preparation of 4,5-dimethoxy-2-nitro-p-toluenesulfonylhydrazone 6.90 g of p-toluenesulfonyl hydrazide was dissolved in 40 ml of ethanol, and 7.90 g of 6-nitroveratraldehyde dissolved in a small amount of ethanol was added thereto. The mixture was stirred at 80° C. for 30 min, cooled to room temperature, and mixed with 100 ml of water. The solid formed therein was filtrated, washed with 100 ml of ethanol, and dried under a reduced pressure, to obtain 12.0 g of the title compound (yield 85%).

$^1$H-NMR(CDCl$_3$) δ: 8.47 (s, 1H), 8.00 (s, 1H), 7.87 (d, 2H), 7.61 (s, 1H), 7.41 (s, 1H), 7.32 (d, 2H), 3.99 (d, 6H), 2.42 (s, 3H)

Step 3: Preparation of 2-(2-4-[5-(4,5-dimethoxy-2-nitro-phenyl)-tetrazol-2-yl]-phenyl-ethyl)-6,7-dimethoxy-1,2,3,4-tetrahydro-isoquinoline 7.4 g of the compound obtained in Step 1 was added to 40 ml of 50% ethanol, and was cooled to 5° C. 6.32 ml of 35% HCl and a solution obtained by dissolving 1.8 g of sodium nitrate in 10 ml of water was added thereto, and the mixture was cooled to −15° C. 9 g of the compound obtained in Step 2 was dissolved in 140 ml of pyridine, and added slowly thereto. The resulting solution was stirred for 14 hours, and washed with 1 N HCl. The organic layer thereof was separated, dried over magnesium sulfate, filtrated, and distilled under a reduced pressure. The residue was purified by column chromatography, to obtain 9.0 g of the title compound (yield 70%).

$^1$H-NMR(CDCl$_3$) δ: 8.08 (d, 2H), 7.66 (s, 1H), 7.45 (d, 2H), 7.32 (s, 1H), 6.59 (d, 2H), 4.03 (s, 6H), 3.85 (s, 6H), 3.68 (s, 2H), 3.01 (m, 2H), 2.84 (m, 6H)

Step 4: Preparation of 2-(2-4-[2-(6,7-dimethoxy-3,4-dihydro-1H-isoquinolin-2-yl)-ethyl]-phenyl-2H-tetrazol-5-yl)-4,5-dimethoxy-phenylamine 0.25 g of the compound obtained in Step 3 was mixed with 3 ml of ethanol, 3 ml of dichloromethane, and 0.07 g of Pd/C, and kept under a hydrogen atmosphere for 12 hours. The reaction mixture was filtrated through a cellite pad, the pad was washed with ethanol, and the filtrate and wash solution were combined and distilled under a reduced pressure, to obtain 0.2 g of the title compound (yield 85%).

$^1$H-NMR(CDCl$_3$) δ: 8.21 (d, 2H), 7.81 (s, 1H), 7.58 (d, 2H), 6.71 (d, 2H), 6.48 (s, 1H), 4.74 (bs, 2H), 4.02 (d, 6H), 3.96 (d, 6H), 3.79 (m, 2H), 3.51 (m, 8H)

Step 5: Preparation of quinoline-3-carbonyl chloride 10 g of 3-quinoline carboxylic acid was mixed with 8.5 ml of thionyl chloride and 150 ml of toluene, and allowed to react at 100° C. for 12 hours. The reaction mixture was condensed under a reduced pressure, to obtain a residue that gave 10 g of the title compound (yield 90%).

$^1$H-NMR(CDCl$_3$) δ: 9.64 (s, 1H), 9.36 (s, 1H), 8.85 (d, 1H), 8.17 (m, 2H), 7.92 (t, 1H)

Step 6: Preparation of quinoline-3-carboxylic acid [2-(2-4-[2-(6,7-dimethoxy-3,4-dihydro-1H-isoquinolin-2-yl)-ethyl]-phenyl-2H-tetrazol-5-yl)-4,5-dimethoxy-phenyl]-amide 0.2 g of the compound obtained in Step 4 was added to 5 ml of dichloromethane, 0.07 g of the compound obtained in Step 5 and 0.1 ml of triethylamine were added thereto, and the mixture was kept at room temperature for 12 hours. After washing with 50 ml of distilled water, the organic layer was dried over magnesium sulfate, filtrated and distilled under a reduced pressure. The residue was subjected to column chromatography to obtain 0.18 g of the title compound (yield 69%).

$^1$H-NMR(CDCl$_3$) δ: 11.86 (s, 1H), 9.69 (s, 1H), 8.95 (s, 1H), 8.75 (s, 1H), 8.23 (d, 1H), 8.12 (d, 1H), 7.99 (d, 1H), 7.86 (t, 2H), 7.66 (m, 1H), 7.46 (d, 2H), 6.59 (d, 2H), 4.06 (d, 6H), 3.85 (s, 6H), 3.69 (s, 2H), 3.04 (m, 2H), 2.83 (m, 6H)

Example 2

Synthesis of quinoline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide 0.15 g of the compound obtained in Step 4 of Example 1 and 0.05 g of quinaldic acid were added to 5 ml of dichloromethane, 0.1 g of 1-(3-dimethylaminopropyl)-3-ethylcarbodiimide hydrochloride and 0.005 g of 4-(dimethylamino)pyridine were added thereto, and the mixture was kept at room temperature for 12 hours. After washing with 50 ml of distilled water, the organic layer was separated and dried over magnesium sulfate, filtrated, and distilled under a reduced pressure. The residue was subjected to column chromatography to obtain 0.14 g of the title compound (yield 73%).

$^1$H-NMR(CDCl$_3$) δ: 12.60 (s, 1H), 8.71 (s, 1H), 8.40 (d, 2H), 8.20 (d, 2H), 8.13 (d, 1H), 7.90 (s, 2H), 7.65 (m, 2H), 7.37 (d, 2H), 6.58 (d, 2H), 4.05 (d, 6H), 3.85 (s, 6H), 3.67 (s, 2H), 3.01 (t, 2H), 2.83 (m, 6H)

Example 3

Synthesis of isoquinoline-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 3-isoquinoline carboxylic acid hydrate instead of quinaldic acid to obtain 0.12 g of the title compound (yield 62%).

$^1$H-NMR(CDCl$_3$) δ: 12.67 (s, 1-H), 9.29 (s, 1H), 8.83 (s, 1H), 8.73 (s, 1H), 8.41 (d, 2H), 8.01 (d, 2H), 7.93 (s, 1H), 7.77 (m, 2H), 7.53 (d, 2H), 6.62 (s, 1H), 6.57 (s, 1H), 4.04 (d, 6H), 3.85 (s, 6), 3.72 (s, 2H), 3.07 (t, 2H), 2.86 (m, 6H)

Example 4

Synthesis of quinoline-8-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 8-quinoline carboxylic acid instead of quinaldic acid, to obtain 0.13 g of the title compound (yield 67%).

$^1$H-NMR(CDCl$_3$) δ: 13.69 (s, 1H), 8.87 (d, 1H), 8.77 (q, 1H), 8.37 (s, 1H), 8.24 (d, 1H), 8.06 (d, 1H), 8.00 (d, 2H), 7.38 (m, 1H), 7.23 (s, 1H), 6.58 (d, 2H), 4.03 (d, 6), 3.85 (s, 6), 3.65 (s, 2), 2.95 (m, 2H), 2.81 (m, 6H)

Example 5

Synthesis of isoquinoline-1-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 1-isoquinoline carboxylic acid instead of quinaldic acid, to obtain 0.12 g of the title compound (yield 62%).

$^1$H-NMR(CDCl$_3$) δ: 12.76 (s, 1H), 9.76 (d, 1H), 8.91 (s, 1H), 8.73 (d, 1H), 8.37 (d, 2H), 8.05 (s, 1H), 8.00 (m, 1H), 7.93 (d, 1H), 7.86 (m, 2H), 7.47 (d, 2H), 6.70 (d, 2H), 4.17 (d, 6H), 3.96 (s, 6H), 3.80 (s, 2H), 3.15 (t, 2H), 2.94 (m, 6H)

Example 6

Synthesis of quinoline-4-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 4-quinoline carboxylic acid instead of quinaldic acid, to obtain 0.11 g of the title compound (yield 57%).

$^1$H-NMR(CDCl$_3$) δ: 11.38 (s, 1H), 9.09 (d, 1H), 8.74 (s, 1H), 8.52 (d, 1H), 8.23 (d, 1H), 7.89 (s, 1H), 7.79 (m, 4H), 7.64 (t, 1H), 7.36 (d, 2H), 6.62 (s, 1H), 6.55 (s, 1H), 4.08 (s, 3H), 4.01 (s, 3H), 3.85 (s, 6H), 3.67 (s, 2H), 2.98 (t, 2H), 2.82 (m, 6H)

Example 7

Synthesis of 4-methoxy-quinoline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-methoxy-phenyl]-amide The procedure of Example 2 was repeated except for using 0.06 g of 4-methoxy-2-quinoline carboxylic acid instead of 0.05 g of quinaldic acid, to obtain 0.15 g of the title compound (yield 76%).

$^1$H-NMR(CDCl$_3$) δ: 12.58 (s, 1H), 8.70 (s, 1H), 8.22 (m, 3H), 8.04 (d, 1H), 7.90 (s, 1H), 7.80 (s, 1H), 7.66 (t, 1H), 7.56 (t, 1H), 7.36 (d, 2H), 6.58 (d, 2H), 4.16 (s, 3H), 4.04 (d, 6H), 3.85 (s, 6H), 3.00 (t, 2H), 2.84 (m, 6H)

Example 8

Synthesis of quinoxaline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 2-quinoxaline carboxylic acid instead of quinaldic acid, to obtain 0.14 g of the title compound (yield 73%).

$^1$H-NMR(CDCl$_3$) δ: 12.45 (s, 1H), 9.75 (s, 1H), 8.65 (s, 1H), 8.14 (m, 4H), 7.79 (m, 3H), 7.37 (d, 2H), 6.54 (d, 2H), 4.00 (d, 2H), 3.81 (s, 6H), 3.64 (s, 2H), 2.98 (t, 2H), 2.79 (m, 6H)

Example 9

Synthesis of pyridine-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.04 g of picolinic acid instead of 0.05 g of quinaldic acid, to obtain 0.13 g of the title compound (yield 73%).

$^1$H-NMR(CDCl$_3$) δ: 12.55 (s, 1H), 8.77 (s, 1H), 8.73 (d, 1H), 8.35 (m, 3H), 7.94 (t, 2H), 7.50 (m, 3H), 6.58 (d, 2H), 4.03 (d, 6H), 3.85 (d, 6H), 3.69 (s, 2H), 3.05 (t, 2H), 2.84 (m, 6H)

Example 10

Synthesis of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-nicotinamide The procedure of Example 2 was repeated except for using 0.04 g of nicotinic acid instead of 0.05 g of quinaldic acid, to obtain 0.12 g of the title compound (yield 67%).

$^1$H-NMR(CDCl$_3$) δ: 11.77 (s, 1H), 9.54 (s, 1H), 8.92 (d, 1H), 8.78 (s, 1H), 8.55 (d, 1H), 8.20 (d, 2H), 7.93 (s, 1H), 7.60 (m, 3H), 6.69 (d, 2H), 4.14 (d, 6H), 3.96 (d, 6H), 3.79 (s, 2), 3.14 (t, 2H), 2.95 (m, 6H)

Example 11

Synthesis of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-isonicotinamide The procedure of Example 2 was repeated except for using 0.04 g of isonicotinic acid instead of 0.05 g of quinaldic acid, to obtain 0.12 g of the title compound (yield 67%).

$^1$H-NMR(CDCl$_3$) δ: 11.73 (s, 1H), 8.86 (m, 2H), 8.67 (s, 1H), 8.10 (d, 2H), 8.00 (d, 2H), 7.83 (s, 1H), 7.49 (d, 2H), 6.58 (d, 2H), 4.00 (d, 6H), 3.85 (s, 6H), 3.68 (s, 2H), 3.03 (t, 2H), 2.85 (m, 6H)

Example 12

Synthesis of pyrazine-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.04 g of 2-pyrazine carboxylic acid instead of 0.05 g of quinaldic acid, to obtain 0.14 g of the title compound (yield 78%).

$^1$H-NMR(CDCl$_3$) δ: 12.47 (s, 1H), 9.56 (d, 1H), 8.83 (d, 1H), 8.73 (s, 1H), 8.70 (m, 1H), 8.30 (d, 2H), 7.93 (s, 1H), 7.52 (d, 2H), 6.59 (d, 2H), 4.05 (d, 6H), 3.86 (d, 6H), 3.70 (2H), 3.06 (t, 2H), 2.85 (m, 6H)

Example 13

Synthesis of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-benzamide The procedure of Example 2 was repeated except for using benzoic acid instead of quinaldic acid, to obtain 0.15 g of the title compound (yield 84%).

$^1$H-NMR(CDCl$_3$) δ: 11.39 (s, 1H), 8.68 (s, 1H), 8.15 (d, 2H), 8.08 (d, 2H), 7.78 (s, 1H), 7.53 (m, 3H), 7.42 (d, 2H), 6.59 (s, 1H), 6.52 (s, 1H), 3.98 (d, 6H), 3.82 (s, 6H), 3.66 (s, 2H), 2.98 (t, 2H), 2.83 (m, 6H)

Example 14

Synthesis of naphthalene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.06 g of 2-naphthoic acid instead of 0.05 g of quinaldic acid, to obtain 0.15 g of the title compound (yield 77%).

$^1$H-NMR(CDCl$_3$) δ: 11.65 (s, 1H), 8.79 (s, 1H), 8.69 (s, 1H), 8.23 (d, 1H), 8.11 (d, 2H), 7.97 (m, 3H), 7.60 (m, 2H), 7.44 (m, 3H), 6.62 (s, 1H), 6.56 (s, 1H), 4.08 (s, 3H), 4.03 (s, 3H), 3.86 (s, 6H), 3.69 (s, 2H), 3.03 (t, 2H), 2.85 (m, 6H)

Example 15

Synthesis of N-[2-2-{4-[2-(6,7-dimethoxy-3,4-dihydro-1H-isoquinolin-2-yl)-ethyl]-phenyl}-2H-tetrazol-5-yl)-4,5-dimethoxy-phenyl]-2-fluoro-benzamide The procedure of Example 2 was repeated except for using 2-fluorobenzoic acid instead of quinaldic acid, to obtain 0.12 g of the title compound (yield 66%).

$^1$H-NMR(CDCl$_3$) δ: 11.23 (s, 1H), 8.58 (s, 1H), 8.08 (m, 3H), 7.84 (s, 1H), 7.52 (m, 1H), 7.44 (d, 2H), 7.32 (t, 1H), 7.23 (m, 1H), 6.62 (s, 1H), 6.55 (s, 1H), 4.03 (d, 6H), 3.85 (s, 6H), 3.67 (s, 2H), 3.01 (t, 2H), 2.85 (m, 6H)

Example 16

Synthesis of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-fluoro-benzamide The procedure of Example 2 was repeated except for using 3-fluorobenzoic acid instead of quinaldic acid, to obtain 0.02 g of the title compound (yield 11%).

$^1$H-NMR(CDCl$_3$) δ: 11.57 (s, 1H), 8.76 (s, 1H), 8.17 (d, 2H), 8.03 (d, 1H), 7.94 (d, 2H), 7.58 (m, 3H), 7.37 (m, 1H), 6.69 (s, 1H), 6.62 (s, 1H), 4.15 (d, 6H), 3.92 (s, 6H), 3.75 (s, 2H), 3.10 (t, 2H), 2.91 (m, 6H)

Example 17

Synthesis of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-4-fluoro-benzamide The procedure of Example 2 was repeated except for using 4-fluorobenzoic acid instead of quinaldic acid, to obtain 0.13 g of the title compound (yield 70%/O).

$^1$H-NMR(CDCl$_3$) δ: 11.41 (s, 1H), 8.60 (s, 1H), 8.12 (m, 2H), 8.06 (d, 2H), 7.76 (s, 1H), 7.48 (d, 2H), 7.19 (t, 2H), 6.59 (s, 1H), 6.51 (s, 1H), 3.98 (d, 6H), 3.82 (s, 6H), 3.68 (s, 2H), 3.03 (t, 2H), 2.84 (m, 6H)

Example 18

Synthesis of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3,4-difluoro-benzamide The procedure of Example 2 was repeated except for using 0.06 g of 3,4-difluorobenzoic acid instead of 0.05 g of quinaldic acid, to obtain 0.12 g of the title compound (yield 63%).

$^1$H-NMR(CDCl$_3$) δ: 11.53 (s, 1H), 8.65 (s, 1H), 8.10 (d, 2H), 7.98 (m, 1H), 7.90 (m, 1H), 7.84 (s, 1H), 7.49 (d, 2H), 7.35 (d, 1H), 6.62 (s, 1H), 6.55 (s, 1H), 4.03 (d, 6H), 3.85 (s, 6H), 3.68 (s, 2H), 3.04 (t, 2H), 2.85 (m, 6H)

Example 19

Synthesis of thiophene-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 3-thiophene carboxylic acid instead of quinaldic acid, to obtain 0.10 g of the title compound (yield 55%).

$^1$H-NMR(CDCl$_3$) δ: 11.43 (s, 1H), 8.63 (s, 1H), 8.21 (d, 1H), 8.08 (d, 2H), 7.76 (s, 1H), 7.74 (s, 1H), 7.48 (d, 2H), 7.38 (m, 1H), 6.61 (s, 1H), 6.54 (s, 1H), 3.99 (d, 6H), 3.83 (s, 6H), 3.67 (s, 2H), 3.02 (t, 2H), 2.83 (m, 6H)

Example 20

Synthesis of furan-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.04 g of 3-furoic acid instead of 0.05 g of quinaldic acid, to obtain 0.11 g of the title compound (yield 62%).

$^1$H-NMR(CDCl$_3$) δ: 11.32 (s, 1H), 8.64 (s, 1H), 8.22 (s, 1H), 8.11 (d, 2H), 7.78 (s, 1H), 7.51 (m, 3H), 7.03 (d, 1H), 6.62 (s, 1H), 6.55 (s, 1H), 4.01 (d, 6H), 3.85 (s, 6H), 3.68 (s, 2H), 3.04 (t, 2H), 2.85 (m, 6H)

Example 21

Synthesis of 4-oxo-4H-chromen-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.07 g of chromone-2-carboxylic acid instead of 0.05 g of quinaldic acid, to obtain 0.16 g of the title compound (yield 80%).

$^1$H-NMR(CDCl$_3$) δ: 12.63 (s, 1H), 8.76 (s, 1H), 8.37 (d, 1H), 8.27 (d, 2H), 7.91 (m, 3H), 7.60 (m, 3H), 7.39 (s, 1H), 6.70 (d, 2H), 4.13 (d, 6H), 3.98 (s, 6H), 3.81 (s, 2H), 3.16 (t, 2H), 2.97 (m, 6H)

Example 22

Synthesis of 6-methyl-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.08 g of 6-methylchromone-2-carboxylic acid instead of 0.05 g of quinaldic acid, to obtain 0.16 g of the title compound (yield 79%/O).
$^1$H-NMR(CDCl$_3$) δ: 12.49 (s, 1H), 8.62 (s, 1H), 8.14 (d, 2H), 8.02 (s, 1H), 7.78 (s, 1H), 7.69 (d, 1H), 7.57 (d, 1H), 7.47 (d, 2H), 6.58 (d, 2H), 4.02 (d, 6H), 3.85 (d, 6H), 3.68 (s, 2H), 3.04 (t, 2H), 2.82 (m, 6H), 2.49 (s, 3H)

Example 23

Synthesis of 5-methoxy-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.3 g of the compound obtained in step 4 of Example 1 and 0.19 g of 5-methoxychromone-2-carboxylic acid instead of 0.15 g of the compound of step 4 of Example 1 and 0.05 g of quinaldic acid, respectively, to obtain 0.23 g of the title compound (yield 55%).
$^1$H-NMR(CDCl$_3$) δ: 12.39 (s, 1H), 8.62 (s, 1H), 8.15 (d, 2H), 7.78 (s, 1H), 7.64 (t, 1H), 7.48 (d, 2H), 7.36 (d, 1H), 7.15 (s, 1H), 6.84 (d, 1H), 6.63 (s, 1H), 6.56 (s, 1H), 4.02 (m, 9H), 3.85 (s, 6H), 3.76 (s, 2H), 3.09 (m, 2H), 2.91 (m, 6H)

Example 24

Synthesis of 6-fluoro-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.3 g of the compound obtained in step 4 of Example 1 and 0.16 g of 6-fluorochromone-2-carboxylic acid instead of 0.15 g of the compound of step 4 of Example 1 and 0.05 g of quinaldic acid, respectively, to obtain 0.27 g of the title compound (yield 66%).
$^1$H-NMR(CDCl$_3$) δ: 12.60 (s, 1H), 8.66 (s, 1H), 8.17 (d, 2H), 7.92 (dd, 1H), 7.87 (dd, 1H), 7.82 (s, 1H), 7.56 (m, 3H), 7.29 (s, 1H), 6.65 (s, 1H), 6.58 (s, 1H), 4.06 (d, 6H), 3.88 (s, 6H), 3.72 (s, 2H), 3.08 (m, 2H), 2.88 (m, 6H)

Example 25

Synthesis of 6-bromo-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.25 g of the compound obtained in step 4 of Example 1 and 0.20 g of 6-bromochromone-2-carboxylic acid instead of 0.15 g of the compound of step 4 of Example 1 and 0.05 g of quinaldic acid, respectively, to obtain 0.22 g of the title compound (yield 60%).
$^1$H-NMR(CDCl$_3$) δ: 12.55 (s, 1H), 8.59 (s, 1H), 8.35 (s, 1H), 8.12 (d, 2H), 7.86 (d, 1H), 7.75 (s, 1H), 7.67 (d, 11, 7.48 (d, 2H), 7.26 (s, 1H), 6.62 (s, 1H), 6.56 (s, 1H), 4.01 (s, 6H), 3.85 (s, 6H), 3.70 (s, 2H), 3.07 (m, 2), 2.86 (m, 6H)

Example 26

Synthesis of cinoline-4-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.3 g of the compound obtained in step 4 of Example 1 and 0.13 g of cinoline-4-carboxylic acid instead of 0.15 g of the compound of step 4 of Example 1 and 0.05 g of quinaldic acid, respectively, to obtain 0.16 g of the title compound (yield 41%).
$^1$H-NMR(CDCl$_3$) δ: 11.64 (s, 1H), 9.79 (s, 1H), 8.73 (s, 1H), 8.67 (dd, 2H), 7.95 (m, 5H), 7.44 (d, 2H), 6.65 (s, 1H), 6.58 (s, 1H), 4.13 (s, 3H), 4.07 (s, 3H), 3.88 (s, 6H), 3.70 (s, 2H), 3.02 (m, 2H), 2.86 (m, 6H)

Example 27

Synthesis of 4-oxo-4H-chromene-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide The procedure of Example 2 was repeated except for using 0.06 g of chromone-3-carboxylic acid instead of 0.05 g of quinaldic acid, to obtain 0.08 g of the title compound (yield 40%).
$^1$H-NMR(CDCl$_3$) δ: 12.15 (s, 1H), 9.04 (s, 1H), 8.89 (d, 1H), 8.50 (d, 2H), 7.60 (m, 3H), 7.49 (m, 3H), 7.04 (s, 1H), 6.55 (s, 1H), 6.54 (s, 1H), 4.04 (d, 6H), 3.84 (s, 6H), 3.67 (s, 2H), 3.03 (m, 2H), 2.84 (m, 6H)

Example 28

Synthesis of quinoline-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-difluoro-phenyl]-amide

Step 1: Preparation of 4,5-difluoro-2-nitro-p-toluenesulfonehydrazone 17.7 g of p-toluenesulfonehydrazide was added to 100 ml of ethanol, 17.7 g of 4,5-difluoro-2-nitro-benzaldehyde was dissolved in a small amount of ethanol, which was added thereto, and the mixture was stirred at 80° C. for 30 min. The reaction mixture was cooled to room temperature, and mixed with 150 ml of water. The precipitated solid was filtrated, washed with 100 ml of ethanol, and dried under a reduced pressure, to obtain 31.6 g of the title compound (yield 94%).
$^1$H-NMR(CDCl$_3$) δ: 11.78 (s, 1H), 8.66 (s, 1H), 7.81 (d, 2H), 7.64 (s, 1H), 7.45 (d, 2H), 7.17 (s, 1H), 2.54 (s, 3H)

Step 2: Preparation of 2-(2-{4-[5-(4,5-difluoro-2-nitro-phenyl)-tetrazol-2-yl]-phenyl}-ethyl)-6,7-dimethoxy-1,2,3,4-tetrahydro-isoquinoline 28.9 g of the compound prepared in Step 1 of Example 1 was added to 100 ml of 50% ethanol, and cooled to 0° C. 25 ml of 35% HCl and 6.6 g of sodium nitrate were added thereto, cooled to −15° C., and 31.6 g of the compound obtained in Step 1 dissolved in 500 ml of pyridine was added slowly thereto. The reaction mixture was stirred for 20 hours, and washed with 1N HCl. The organic layer resulting therefrom was separated, dried over magnesium sulfate, filtrated, distilled under a reduced pressure, and recrystallized using ethyl acetate, to obtain 28 g of the title compound (yield 60%).

$^1$H-NMR(CDCl$_3$) δ: 8.10 (d, 2H), 7.67 (s, 1H), 7.48 (d, 2H), 7.42 (s, 1H), 6.61 (d, 2), 3.98 (s, 6H), 3.77 (s, 2H), 3.00 (m, 2H), 2.85 (m, 6H)

Step 3: Preparation of 2-(2-4-[2-(6,7-dimethoxy-3,4-dihydro-1H-isoquinolin-2-yl)-ethyl]-phenyl-2H-tetrazol-5-yl)-4,5-difluoro-phenylamine 28 g of the compound obtained in Step 2 was mixed with a mixture of 360 ml of ethanol and 360 ml of dichloromethane, 8.4 g of Pd/C was added thereto, and the mixture was kept under an atmospheric hydrogen for 18 hours. The reduction mixture was filtrated through a cellite pad, the pad was washed with ethanol, the filtrate and the washed solution were combined and condensed under a reduced pressure, to obtain a residue that gave 22 g of the title compound (yield 84%).

$^1$H-NMR(CDCl$_3$) ° C.: 8.24 (d, 2H), 7.88 (s, 1H), 7.61 (d, 2H), 6.75 (d, 2H), 6.49 (s, 1H), 4.79 (bs, 2H), 3.99 (d, 6H), 3.81 (m, 2), 3.54 (m, 8H)

Step 4: Preparation of quinoline-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-difluoro-phenyl]-amide 1.0 g of the compound obtained in Step 3 was mixed with 15 ml of dichloromethane, 0.47 g of the compound obtained in Step 5 of Example 1 and 0.4 ml of triethylamine were added thereto, and the mixture was stirred at room temperature for 20 hours. After washing with 100 ml of distilled water, the resulting organic layer was dried over magnesium sulfate, filtrated, and distilled under a reduced pressure. The residue obtained thus was subjected to column chromatography to obtain 0.8 g of the title compound (yield 61%).

$^1$H-NMR(CDCl$_3$)° C.: 11.84 (S, 1H), 9.70 (s, 1H), 8.97 (s, 1H), 8.81 (s, 1H), 8.22 (d, 1H), 8.19 (d, 1H), 7.97 (d, 1H), 7.89 (t, 2H), 7.68 (m, 1H), 7.48 (d, 2H), 6.61 (d, 2H), 4.01 (d, 6H), 3.68 (s, 2H), 3.08 (m, 2H), 2.85 (m, 6H)

Example 29

Synthesis of quinoline-3-carboxylic acid [2-(2-{4-[2-(6,7-dimethoxy-3,4-dihydro-1H-isoquinolin-2-yl)-ethylsulfanyl]-phenyl}-2H-tetrazol-5-yl)-4,5-dimethoxy-phenyl]-amide Step 1: Preparation of 1-(2-bromo-ethylsulfanyl)-4-nitro-benzene 6.94 ml of 1,2-dibromoethane was diluted with 100 ml of acetonitrile, mixed with 11.2 g of potassium carbonate and 5.0 g of 4-nitro-benzenethiol, and stirred at 80° C. for 18 hours. After washing with 300 ml of distilled water and with 300 ml of aqueous NaCl, the resulting organic layer was dried over magnesium sulfate, filtrated, and distilled under a reduced pressure. The residue obtained thus was subjected to column chromatography to obtain 6.9 g of the title compound (yield 82%).

$^1$H-NMR(CDCl$_3$) δ: 7.60 (s, 2H), 7.42 (s, 2H), 2.92 (m, 4H)

Step 2: Preparation of 4-[2-(6,7-dimethoxy-3,4-dihydro-1H-isoquinolin-2-yl)-ethylsulfanyl]phenylamine 6.9 g of the compound obtained in Step 1, 6.1 g of 6,7-dimethoxy-1,2,3,4-tetrahydroisoquinoline hydrochloride and 7.7 g of potassium carbonate were added to 80 ml of acetonitrile, and stirred at 80° C. for 14 hours. After washing with 250 ml of distilled water and with 300 ml of aqueous NaCl, the resulting organic layer was dried over MgSO$_4$, filtrated, and distilled under a reduced pressure to obtain 5.3 g of 6,7-dimethoxy-2-[2-(4-nitro-phenylsulfanyl)-ethyl]-1,2,3,4-tetrahydro-isoquinoline. The compound was stirred with 3.4 g of Iron, 6.74 ml of 35% HCl and 35 ml of methanol under 1 atmospheric nitrogen atmosphere for 20 hours. The reaction mixture was filtrated through a cellite pad, the pad was washed with methanol, and the filtrate and wash solution were combined, and distilled under a reduced pressure to obtain a residue that gave 3.0 g of the title compound (yield 33%).

$^1$H-NMR(CDCl$_3$) δ: 7.58 (s, 2H), 7.32 (s, 2H), 6.61 (s, 1H), 6.55 (s, 1H), 4.01 (s, 6H), 3.84 (d, 6H), 3.68 (s, 2H), 3.26 (m, 2H), 2.83 (m, 61

Step 3: Preparation of 2-(2-{4-[5-(4,5-dimethoxy-2-nitro-phenyl)-tetrazol-2-yl]-phenylsulfanyl}-ethyl)-6,7-dimethoxy-1,2,3,4-tetrahydro-isoquinoline 0.8 g of the compound obtained in Step 2 was added to 4 ml of 50% ethanol. After cooling to 0° C., 0.6 ml of 35% HCl and 0.16 g of sodium nitrate were added thereto, and after cooling to −15° C., a solution of 0.9 g of the compound obtained in Step 2 of Example 1 dissolved in 14 ml of pyridine was added slowly thereto. The mixture was stirred for 20 hours, washed with 1 N HCl, dried over magnesium sulfate, filtrated, and distilled under a reduced pressure. The resulting residue was subjected to column chromatography to obtain 0.7 g of the title compound (yield 52%).

$^1$H-NMR(CDCl$_3$) δ: 8.08 (d, 2H), 7.58 (s, 1H), 7.50 (d, 2H), 7.32 (s, 1H), 6.60 (s, 1H), 6.53 (s, 1H), 4.04 (s, 6H), 3.85 (d, 6H), 3.66 (s, 2H), 3.25 (m, 2H), 2.85 (m, 6H)

Step 4: Preparation of 2-(2-{4-[2-(6,7-dimethoxy-3,4-dihydro-1H-isoquinolin-2-yl)-ethylsulfanyl]-phenyl}-2H-tetrazol-5-yl)-4,5-dimethoxy-phenylamine 0.2 g of the compound obtained in Step 3, 0.1 g of Iron and 0.15 ml of concentrated HCl were added to 3 ml of methanol, and stirred under 1 atmospheric hydrogen atmosphere for 18 hours. The reaction mixture was filtrated through a cellite pad, the pad was washed with methanol, the filtrate and wash solution were combined, and distilled under a reduced pressure to obtain a residue that gave 0.15 g of the title compound (yield 79%).

$^1$H-NMR(CDCl$_3$) δ: 8.14 (d, 2H), 7.74 (s, 1H), 7.56 (d, 2H), 6.65 (s, 1H), 6.56 (s, 1H), 6.40 (s, 1H), 3.96 (d, 6H), 3.88 (s, 6H), 3.69 (s, 2H), 3.30 (m, 2H), 2.88 (m, 6H)

Step 5: Preparation of quinoline-3-carboxylic acid [2-(2-{4-[2-(6,7-dimethoxy-3,4-dihydro-1H-isoquinolin-2-yl)-ethylsulfanyl]-phenyl}-2H-tetrazol-5-yl)-4,5-dimethoxy-phenyl]-amide The procedure of Example 2 was repeated except for using 0.15 g of the compound obtained in Step 4 and 0.06 g of 3-isoquinoline carboxylic acid hydrate as starting materials to obtain 0.10 g of the title compound (yield 52%).

¹H-NMR(CDCl₃) δ: 11.84 (s, 1H), 9.70 (d, 1H), 8.96 (d, 1H), 8.75 (s, 1H), 8.24 (d, 1H), 8.12 (d, 2H), 8.01 (d, 1H), 7.88 (m, 2H), 7.70 (t, 1H), 7.51 (d, 2H), 6.64 (s, 1H), 6.56 (s, 1H), 4.08 (d, 3H), 4.04 (d, 3H), 3.86 (s, 6H), 3.69 (s, 2H), 3.29 (m, 2H), 2.88 (m, 6H)

Example 30

Synthesis of N-2-(2-(4(2-(6,7-dimethoxy-3,4-dihydro isoquinolin-2(1H)-2-yl)-ethyl)phenyl)-2H-tetrazol-5-yl)-4,5-dimethoxy-phenyl)quinoline-3-carboxamide]

Step 1: Preparation of 2-(2-bromo-ethyl)-6,7-dimethoxy-1,2,3,4-tetrahydro-isoquinoline 1 g of 6,7-dimethoxy-1,2,3,4-tetrahydroisoquinoline hydrochloride was mixed with 15 ml of N,N-dimethylformamide, 1.05 g of 1,3-dibromoethane, 1.80 g of potassium carbonate and 0.6 g of potassium iodide were added thereto, and the mixture was stirred at 100° C. for 6 hours. The reaction mixture was extracted with 250 ml of ethylacetate and the extract was washed with 250 ml of distilled water. The resulting organic layer was dried magnesium sulfate, and filtrated under a reduced pressure to remove the solvent. The residue obtained thus was subjected to column chromatography to obtain 1 g of the title compound (yield 60%).

¹H-NMR(CDCl₃): 6.52 (d, 2H), 3.85 (s, 6H), 3.59 (s, 2H), 2.93-2.81 (m, 4H), 2.77-2.68 (m, 2H), 2.64-2.56 (m, 2H)

Step 2: Preparation of 5-(4,5-dimethoxy-2-nitro-phenyl)-2H-tetrazole 2.33 g of 4,5-dimethoxy-2-nitro-benzonitrile was added to 15 ml of toluene, 0.28 g of dibutyltinoxide and 2.58 g of trimethylsilyl azide was added thereto, and the mixture was stirred at 100° C. for 16 hours. The reaction mixture was distilled under a reduced pressure to remove the solvent, and the resulting solid was washed with 250 ml of dichloromethane to obtain 2.0 g of the title compound as a grey solid (yield 71%).

¹H-NMR(CD₃OD): 7.90 (s, 1H), 7.30 (s, 1H), 4.04 (s, 3), 3.99 (s, 3H)

Step 3: Preparation of 2-[2-(6,7-dimethoxy-3,4-dihydro-1H-isoquinolin-2-yl-ethyl)-2H-tetrazol-5-yl]4,5-dimethoxy-phenylamine 0.25 g of the compound obtained in Step 2, 0.3 g of the compound obtained in Step 1 and 0.17 ml of triethylamine were added to 10 ml of dichloromethane, and stirred for 16 hours. The reaction mixture was extracted with 250 ml of ethylacetate and the extract was washed with 250 ml of distilled water. The resulting organic layer was dried magnesium sulfate, and filtrated under a reduced pressure, which was subjected to column chromatography to obtain 0.1 g of a nitro derivative. The nitro derivative was mixed with 30 ml of dichloromethane, 30 ml of ethanol and 0.10 g of Pd/C, and kept under 1 atmospheric hydrogen atmosphere for 18 hours. The reduction mixture was filtrated through a cellite pad under a reduced pressure, the pad was washed with methanol, the filtrate and the wash solution were combined, and distilled under a reduced pressure to obtain a residue which gave 0.40 g of the title compound (yield 91%).

¹H-NMR(CD₃OD): 7.37 (s, 1H), 6.59 (s, 1H), 6.52 (s, 1H), 6.47 (s, 1H), 4.00 (s, 2H), 3.80 (s, 3), 3.79 (s, 3H), 3.77 (s, 3), 3.76 (s, 3H), 2.80-2.70 (m, 2H), 2.65-3.1 (m, 6H)

Step 4: Preparation of quinoline-3-carboxylic acid N-(2-(2-(4-(2-(6,7-dimethoxy-3,4-dihydroisoquinolin-2(1H)-2-yl)-ethyl)phenyl)-2H-tetrazol-5-yl)-4,5-dimethoxy-phenyl)quinoline-3-carboxamide]

The procedure of Example 2 was repeated except for using 0.40 g of the compound obtained in Step 3 and 0.22 g of 3-quinoline carboxylic acid as starting materials to obtain 0.30 g of the title compound (yield 56%).

¹H-NMR(CDCl₃): 9.30 (s, 1H), 8.80 (s, 1H), 8.20 (m, 1H), 8.15 (d, 1H), 7.90 (t, 2H), 7.80 (t, 1H), 7.53 (s, 1H), 6.60 (s, 1H), 6.55 (s, 1H), 4.01 (s, 2H), 3.80 (s, 6H), 3.70 (s, 6H), 3.7-3.5 (m, 8H)

Example 31

Synthesis of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-phenyl-acrylamide The procedure of Example 2 was repeated except for using 0.15 g of the compound obtained in Step 4 of Example 1 and 0.05 g of trans-cinnamic acid as starting materials to obtain 0.11 g of the title compound (yield 59%).

¹H-NMR(CDCl₃) δ: 11.07 (s, 1H), 8.82 (s, 1H), 8.10 (m, 4H), 7.83 (s, 1H), 7.79 (s, 1H), 7.58 (s, 1H), 7.50 (s, 1H), 7.41 (s, 1H), 7.31 (d, 1H), 6.71 (s, 1H), 6.68 (s, 1H), 6.62 (s, 1H), 6.55 (s, 1H), 3.98 (d, 6H), 3.85 (s, 6H), 3.69 (s, 2H), 3.01 (t, 2H), 2.83 (m, 6H)

Example 32

Synthesis of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-quinolin-3-yl-acrylamide Step 1: Preparation of 3-quinolin-3-yl-acrylic acid 80 g of 3-quinoline carboxaldehyde, 85 g of malonic acid and 6.50 g of piperidine were added to 350 ml of pyridine, and stirred at 100° C. for 3 hours. After mixing with 1000 ml of distilled water, concentrated HCl was added thereto until pH of the solution became 4.8, and stirred for 1 hour. The resulting solid was filtrated under a reduced pressure, washed with 1500 ml of distilled water, and dried for 15 to 40 hours to obtain 96 g of the title compound as a white solid (yield 95%).

¹H-NMR(DMSO-d₆): 9.23 (s, 1H), 8.67 (s, 1H), 8.04-7.98 (m, 2H), 7.82-7.75 (m, 2H), 7.64 (t, 1H), 6.85 (d, 1H)

Step 2: Preparation of N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-quinolin-3-yl-acrylamide The procedure of Example 2 was repeated except for using 0.22 g of the compound obtained in Step 4 of Example 1 and 0.10 g of the compound obtained in Step 1 as starting materials to obtain 0.18 g of the title compound (yield 61%).

¹H-NMR(CDCl₃): 9.09 (s, 1H), 8.22 (s, 1H), 7.89-7.84 (m, 2H), 7.77-7.71 (m, 3H), 7.60-7.56 (m, 3H), 7.26-7.19 (m, 3H), 6.81 (m, 2H), 6.61 (s, 1H), 6.55 (s, 1H), 3.96 (s, 6H), 3.88 (s, 6H), 3.68 (s, 2H), 2.99-2.77 (m, 8H)

Example 33

Synthesis of 4-oxo-4H-chromene-2-carboxylic acid (2-{2-[4-(2-{[2-(3,4-dimethoxy-phenyl)-ethyl]-methyl-amino}-ethyl)-phenyl]-2H-tetrazol-5-yl}-4,5-dimethoxy-phenyl)-amide

Step 1: Preparation of 4-(2-{[2-(3,4-dimethoxy-phenyl)-ethyl]-methyl-amino}-ethyl)-phenylamine 7.0 g of 2-(4-nitrophenyl)ethyl bromide, 5.94 g of [2-(3,4-dimethoxy-phenyl)-ethyl]-methyl-amine, 8.41 g of potassium carbonate and 4.56 g of sodium iodide were added to 70 ml of N,N-dimethylformamide, and kept at 100° C. for 6 hours. After mixing with 100 ml of distilled water, the reaction mixture was extracted three times with 200 ml portion of ethylacetate, and the combined organic layer was washed with saturated NaCl, dried over magnesium sulfate, filtrated under a reduced pressure, and distilled to remove the solvent. The residue obtained thus was recrystallized from ethyl acetate to obtain 7.86 g of a nitro derivative. The nitro derivative was mixed with 200 ml of tetrahydrofuran and 200 ml of methanol, 0.5 g of Pd/C was added thereto, and the mixture was kept under 1 atmospheric hydrogen atmosphere for 18 hours. The reduction mixture was filtrated through a cellite pad under a reduced pressure, the pad was washed with methanol, the filtrate and wash solution were combined, and distilled under a reduced pressure to obtain a residue that gave 6.52 g of the title compound (yield 68%).

$^1$H-NMR(CDCl$_3$) δ: 7.35 (d, 1H), 6.90 (d, 2H), 6.67 (d, 2H), 6.60 (d, 1H), 6.54 (s, 1H), 3.90 (s, 6H), 3.86 (s, 6H), 2.95-2.71 (m, 8H), 2.35 (s, 3H)

Step 2: Preparation of 2-{2-[4-(2-{[2-(3,4-dimethoxy-phenyl)-ethyl]-methyl-amino}-ethyl)-phenyl]-2H-tetrazol-5-yl}-4,5-dimethoxy-phenylamine The procedure of Step 3 and 4 of Example 1 was repeated except for using 1.2 g of the compound obtained in Step 2 of Example 1 and 1 g of the compound obtained in Step 1 as starting materials to obtain 0.98 g of the title compound (yield 70%).

$^1$H-NMR(CDCl$_3$) δ: 7.70-7.66 (m, 1H), 7.62-7.52 (m, 3H), 7.45-7.20 (m, 2H), 6.93 (d, 1H), 6.70 (s, 1H), 6.55 (s, 1H), 3.98 (s, 6H), 3.85 (s, 6H), 2.93-2.73 (m, 8H), 2.43 (s, 3H)

Step 3: Preparation of 4-oxo-4H-chromene-2-carboxylic acid (2-{2-[4-(2-{[2-(3,4-dimethoxy-phenyl)-ethyl]-methyl-amino}-ethyl)-phenyl]-2H-tetrazol-5-yl}-4,5-dimethoxy-phenyl)-amide The procedure of Example 2 was repeated except for using 1 g of the compound obtained in Step 2 and 0.97 g of chromone-2-carboxylic acid as starting materials to obtain 0.99 g of the title compound (yield 75%).

$^1$H-NMR(CDCl$_3$) δ: 7.70-7.63 (m, 1H), 7.62-7.51 (m, 3H), 7.45-7.18 (m, 2H), 6.93 (d, 1H), 6.68 (s, 1H), 6.53 (s, 1H), 3.97 (s, 6H), 3.86 (s, 6H), 2.95-2.75 (m, 8H), 2.44 (s, 3H)

The compounds prepared in Example 1 to 33 are listed in Table I.

TABLE I

| Ex. No. | $R_1$ | $R_2$ | $R_3$ | $R_4$ | $R_5$ | $R_6$ | $R_7$ | $R_8$ | $R_9$ | $R_{10}$ | $R_{11}$ | X | m | n |
|---|---|---|---|---|---|---|---|---|---|---|---|---|---|---|
| 1 | quinolin-3-carboxylate | H | OCH$_3$ | OCH$_3$ | H | CH$_2$—CH$_2$ | H | OCH$_3$ | OCH$_3$ | H | CH$_2$ | 1 | 1 |
| 2 | quinolin-2-carboxylate | H | OCH$_3$ | OCH$_3$ | H | CH$_2$—CH$_2$ | H | OCH$_3$ | OCH$_3$ | H | CH$_2$ | 1 | 1 |
| 3 | isoquinolin-3-carboxylate | H | OCH$_3$ | OCH$_3$ | H | CH$_2$—CH$_2$ | H | OCH$_3$ | OCH$_3$ | H | CH$_2$ | 1 | 1 |
| 4 | quinolin-8-carboxylate | H | OCH$_3$ | OCH$_3$ | H | CH$_2$—CH$_2$ | H | OCH$_3$ | OCH$_3$ | H | CH$_2$ | 1 | 1 |
| 5 | isoquinolin-1-carboxylate | H | OCH$_3$ | OCH$_3$ | H | CH$_2$—CH$_2$ | H | OCH$_3$ | OCH$_3$ | H | CH$_2$ | 1 | 1 |
| 6 | quinolin-4-carboxylate | H | OCH$_3$ | OCH$_3$ | H | CH$_2$—CH$_2$ | H | OCH$_3$ | OCH$_3$ | H | CH$_2$ | 1 | 1 |
| 7 | 4-methoxyquinolin-2-carboxylate | H | OCH$_3$ | OCH$_3$ | H | CH$_2$—CH$_2$ | H | OCH$_3$ | OCH$_3$ | H | CH$_2$ | 1 | 1 |
| 8 | quinoxalin-2-carboxylate | H | OCH$_3$ | OCH$_3$ | H | CH$_2$—CH$_2$ | H | OCH$_3$ | OCH$_3$ | H | CH$_2$ | 1 | 1 |
| 9 | pyridin-2-carboxylate | H | OCH$_3$ | OCH$_3$ | H | CH$_2$—CH$_2$ | H | OCH$_3$ | OCH$_3$ | H | CH$_2$ | 1 | 1 |
| 10 | nicotinate | H | OCH$_3$ | OCH$_3$ | H | CH$_2$—CH$_2$ | H | OCH$_3$ | OCH$_3$ | H | CH$_2$ | 1 | 1 |
| 11 | isonicotinate | H | OCH$_3$ | OCH$_3$ | H | CH$_2$—CH$_2$ | H | OCH$_3$ | OCH$_3$ | H | CH$_2$ | 1 | 1 |
| 12 | pirazin-2-carboxylate | H | OCH$_3$ | OCH$_3$ | H | CH$_2$—CH$_2$ | H | OCH$_3$ | OCH$_3$ | H | CH$_2$ | 1 | 1 |
| 13 | benzonate | H | OCH$_3$ | OCH$_3$ | H | CH$_2$—CH$_2$ | H | OCH$_3$ | OCH$_3$ | H | CH$_2$ | 1 | 1 |
| 14 | naphthalen-2-carboxylate | H | OCH$_3$ | OCH$_3$ | H | CH$_2$—CH$_2$ | H | OCH$_3$ | OCH$_3$ | H | CH$_2$ | 1 | 1 |
| 15 | 2-fluorobenzonate | H | OCH$_3$ | OCH$_3$ | H | CH$_2$—CH$_2$ | H | OCH$_3$ | OCH$_3$ | H | CH$_2$ | 1 | 1 |
| 16 | 3-fluorobenzonate | H | OCH$_3$ | OCH$_3$ | H | CH$_2$—CH$_2$ | H | OCH$_3$ | OCH$_3$ | H | CH$_2$ | 1 | 1 |
| 17 | 4-fluorobenzonate | H | OCH$_3$ | OCH$_3$ | H | CH$_2$—CH$_2$ | H | OCH$_3$ | OCH$_3$ | H | CH$_2$ | 1 | 1 |
| 18 | 3,4-difluorobenzonate | H | OCH$_3$ | OCH$_3$ | H | CH$_2$—CH$_2$ | H | OCH$_3$ | OCH$_3$ | H | CH$_2$ | 1 | 1 |
| 19 | thiophen-3-carboxylate | H | OCH$_3$ | OCH$_3$ | H | CH$_2$—CH$_2$ | H | OCH$_3$ | OCH$_3$ | H | CH$_2$ | 1 | 1 |
| 20 | puran-3-carboxylate | H | OCH$_3$ | OCH$_3$ | H | CH$_2$—CH$_2$ | H | OCH$_3$ | OCH$_3$ | H | CH$_2$ | 1 | 1 |
| 21 | 4-oxo-4H-chromen-2-carboxylate | H | OCH$_3$ | OCH$_3$ | H | CH$_2$—CH$_2$ | H | OCH$_3$ | OCH$_3$ | H | CH$_2$ | 1 | 1 |
| 22 | 6-methyl-4-oxo-4H-chromen-2-carboxylate | H | OCH$_3$ | OCH$_3$ | H | CH$_2$—CH$_2$ | H | OCH$_3$ | OCH$_3$ | H | CH$_2$ | 1 | 1 |
| 23 | 5-methoxy-4-oxo-4H-chromen-2-carboxylate | H | OCH$_3$ | OCH$_3$ | H | CH$_2$—CH$_2$ | H | OCH$_3$ | OCH$_3$ | H | CH$_2$ | 1 | 1 |
| 24 | 6-fluoro-4-oxo-4H-chromen-2-carboxylate | H | OCH$_3$ | OCH$_3$ | H | CH$_2$—CH$_2$ | H | OCH$_3$ | OCH$_3$ | H | CH$_2$ | 1 | 1 |
| 25 | 6-bromo-4-oxo-4H-chromen-2-carboxylate | H | OCH$_3$ | OCH$_3$ | H | CH$_2$—CH$_2$ | H | OCH$_3$ | OCH$_3$ | H | CH$_2$ | 1 | 1 |
| 26 | sinolin-4-carboxylate | H | OCH$_3$ | OCH$_3$ | H | CH$_2$—CH$_2$ | H | OCH$_3$ | OCH$_3$ | H | CH$_2$ | 1 | 1 |
| 27 | 4-oxo-4H-chromen-3-carboxylate | H | OCH$_3$ | OCH$_3$ | H | CH$_2$—CH$_2$ | H | OCH$_3$ | OCH$_3$ | H | CH$_2$ | 1 | 1 |
| 28 | quinolin-3-carboxylate | H | F | F | H | CH$_2$—CH$_2$ | H | OCH$_3$ | OCH$_3$ | H | CH$_2$ | 1 | 1 |
| 29 | quinolin-3-carboxylate | H | OCH$_3$ | OCH$_3$ | H | CH$_2$—CH$_2$ | H | OCH$_3$ | OCH$_3$ | H | S | 2 | 1 |
| 30 | quinolin-3-carboxylate | H | OCH$_3$ | OCH$_3$ | H | CH$_2$—CH$_2$ | H | OCH$_3$ | OCH$_3$ | H | CH$_2$ | 1 | 1 |
| 31 | 3-phenyl-acrylate | H | OCH$_3$ | OCH$_3$ | H | CH$_2$—CH$_2$ | H | OCH$_3$ | OCH$_3$ | H | CH$_2$ | 1 | 1 |
| 32 | 3-quinolin-3-yl-acrylate | H | OCH$_3$ | OCH$_3$ | H | CH$_2$—CH$_2$ | H | OCH$_3$ | OCH$_3$ | H | CH$_2$ | 1 | 1 |
| 33 | 4-oxo-4H-chromen-2-carboxylate | H | OCH$_3$ | OCH$_3$ | H | CH$_3$ | H | H | OCH$_3$ | OCH$_3$ | H | CH$_2$ | 1 | 1 |

Example 34

Synthesis of quinoline-3-carboxylic acid [2-(2-4-[2-(6,7-dimethoxy-3,4-dihydro-1H-isoquinolin-2-yl)-ethyl]-phenyl-2H-tetrazol-5-yl)-4,5-dimethoxy-phenyl]-amide methanesulfonate 1 g of the compound obtained in Example 1 was stirred with 70 ml of methanol for 30 min, and a mixture of 0.1 ml of methanesulfonic acid and 5 ml of methanol, was added dropwise thereto at 0° C. The mixture was heated to room temperature for 10 min, and stirred for 6 hours, which gave 0.95 g of the title compound (yield 83%).
$^1$H-NMR(CD$_3$OD) δ: 9.71 (s, 1H), 9.55 (s, 1H), 8.33 (d, 1H), 8.31 (d, 1H), 8.24-8.20 (m, 3H), 8.10 (t, 1H), 7.89 (s, 1H), 7.65 (m, 3H), 6.86 (s, 1H), 6.84 (s, 1H), 4.00 (d, 6H), 3.86 (d, 6H), 3.65-3.55 (m, 4H), 3.37-3.26 (m, 6H), 2.19 (s, 3H)

Example 35

Synthesis of 4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide methanesulfonate The procedure of Example 33 was repeated except for using 1.2 g of the compound obtained in Example 21 and 0.12 ml of methanesulfonic acid as starting materials to obtain 1.1 g of the title compound (yield 80%).
$^1$H-NMR(CD$_3$OD) δ: 8.35 (s, 1H), 8.18-8.16 (m, 3H), 7.95 (t, 1H), 7.79 (d, 1H), 7.71-7.64 (m, 4H), 7.08 (s, 1H), 7.05 (s, 1H), 7.01 (s, 1H), 4.05 (s, 6H), 4.01 (s, 3H), 3.90 (s, 3H), 3.90-3.73 (m, 4H), 3.51-3.41 (m, 6H), 2.18 (s, 3H)

Example 36

Synthesis of 4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide hydrochloride The procedure of Example 33 was repeated except for using 1.5 g of the compound obtained in Example 21 and 0.1 ml of hydrochloric acid as starting materials to obtain 1.4 g of the title compound (yield 89%).
$^1$H-NMR(CD$_3$OD) δ: 8.37 (s, 1H), 8.19-8.15 (m, 3H), 7.97 (t, 1H), 7.82 (d, 1H), 7.73-7.65 (m, 4H), 7.18 (s, 1H), 7.15 (s, 1H), 7.11 (s, 1H), 4.07 (s, 6H), 4.02 (s, 3H), 3.98 (s, 3H), 3.94-3.75 (m, 2H), 3.52-3.43 (m, 8H)

Preparation Example 1

Formulation of Preparation for Oral Administration

A tablet was prepared using the following ingredients, wherein the active ingredient was the compound of Example 21:

| Ingredient | Quantity(mg/tablet) |
|---|---|
| Active ingredient | 100 |
| Corn starch | 80 |
| Lactose | 80 |
| Magnesium stearate | 5 |

Other tablets were also prepared by the same method using each of the inventive tetrazole derivatives of Example from 1 to 20 and from 22 to 36 as an active ingredient. At a case of the compound of Example 35, the amount used was 114 mg.

Preparation Example 2

Formulation of Preparation for Oral Administration

A hard gelatin capsule was prepared using the following ingredients, wherein the active ingredient was the compound of Example 21:

| Ingredient | Quantity(mg/capsule) |
|---|---|
| Active ingredient | 100 |
| Corn starch | 40 |
| Lactose | 80 |
| Crystalline cellulose | 80 |
| Magnesium stearate | 5 |

Other capsules were also prepared by the same method using each of the inventive tetrazole derivatives of Example from 1 to 20 and from 22 to 36 as an active ingredient. At a case of the compound of Example 35, the amount used was 114 mg.

Preparation Example 3

Formulation of Preparation for Injection

An injective preparation was prepared using the following ingredients, wherein the active ingredient was the compound of Example 21:

| Ingredient | Quantity(mg/capsule) |
|---|---|
| Active ingredient | 20 mg |
| 5% glucose solution | 10 ml |
| HCl (1N) | (amount that the pH of the resulting solution becomes 4) |

Other injective preparations were also prepared by the same method using each of the inventive tetrazole derivatives of Example from 1 to 20 and from 22 to 36 as an active ingredient. At a case of the compound of Example 35, the amount used was 23 mg and HCl was not used.

Preparation Example 4

Formulation of Preparation for Injection

An injective preparation was prepared using the following ingredients, wherein the active ingredient was the compound of Example 21:

| Ingredient | Quantity(mg/capsule) |
|---|---|
| Active ingredient | 20 mg |
| Polyethyleneglycol 400 | 2 ml |
| Sterile water | 8 ml |

Other injective preparations were also prepared by the same method using each of the inventive tetrazole derivatives of Example from 1 to 20 and from 22 to 36 as an active ingredient. At a case of the compound of Example 35, the amount used was 23 mg.

Test Example 1

Inhibition Activity of Inventive Compound Against p-Glycoprotein

In order to investigate the bioavailability each of the inventive compounds as an inhibitor of p-glycoprotein, its cellular toxicity was measured using MCF-7 cell and MCF-7/Dox cell, which is MCF-7 expressing p-glycoprotein.

The cells were subcultured in 5% FBS (fetal bovine serum)/RPMI1640 medium supplemented with glutamine 2 mmol, sodium bicarbonate 3.7 g/L and gentamicin 10 mg/L at 37° C. in 5% $CO_2$ incubator under 100% humidity, and collected using a 0.25% trypsin solution containing 3 mM 1,2-cyclohenxandiamine tetraacetic acid.

The collected cells were plated on a 96 well flat-bottomed plate at a density of $2 \times 10^3$ cells/well, and incubated in the same medium for 24 hours. Paclitaxel, an anticancer agent, was diluted with the same medium to obtain $10^{-11} \sim 10^{-6}$ M test solutions. After removing the culture media, each well was treated with 100 ul of a test solution, alone or in combination with 50 nM each of the test compounds of Examples 1 to 30. After incubating for 72 hours, the culture medium was removed, each well was treated with 10% trichloroacetic acid for 1 hour to fix the cells, washed with water, and dried at room temperature. After adding a dyeing solution containing 1% acetic acid with 0.4% SRB (sulforhodamine B) thereto, the wells were kept at room temperature for 30 min, and washed with 1% acetic acid to remove remaining SRB. 10 ml of trisma base solution having pH 10.3~10.5 was added thereto, and the absorbance at 520 nm of each well was measured using a microplate reader to evaluate $ED_{50}$, the drug concentration at which the growth of the cancer cells was inhibited to the extent of 50%. Also, the enhancement of the anticancer activity of paclitaxel against MCF7/Dox (resistant cancer cells) was measured by determining $ED^{PAC}_{50}/ED_{50}$, wherein $ED^{PAC}_{50}$ is the value determined for the case of paclitaxel alone. The results are shown in Table II.

TABLE II

| Compound | $ED_{50}$ (nM) | | $ED_{50}^{PAC}/ED_{50}$ |
|---|---|---|---|
| | MCF7 | MCF7/Dox | |
| Control | 11.5 | 294.6 | 1.0 |
| Example 1 | 7.9 | 14.5 | 20.3 |
| Example 2 | 12.1 | 109.9 | 2.7 |
| Example 3 | 8.5 | 83.8 | 3.5 |
| Example 4 | 5.4 | 69.2 | 4.3 |
| Example 5 | 7.6 | 162.0 | 1.8 |
| Example 6 | 9.1 | 88.6 | 3.3 |
| Example 7 | 7.4 | 90.0 | 3.3 |
| Example 8 | 6.2 | 13.4 | 22.0 |

TABLE II-continued

| Compound | $ED_{50}$ (nM) | | $ED_{50}^{PAC}/ED_{50}$ |
|---|---|---|---|
| | MCF7 | MCF7/Dox | |
| Example 9 | 8.7 | 94.8 | 3.1 |
| Example 10 | 9.1 | 97.9 | 3.0 |
| Example 11 | 7.2 | 93.2 | 3.2 |
| Example 12 | 9.1 | 97.9 | 3.0 |
| Example 13 | 7.7 | 86.9 | 3.4 |
| Example 14 | 10.3 | 112.7 | 2.6 |
| Example 15 | 11.5 | 71.3 | 4.1 |
| Example 16 | 7.9 | 44.3 | 6.7 |
| Example 17 | 10.2 | 73.1 | 4.0 |
| Example 18 | 10.3 | 80.4 | 3.7 |
| Example 19 | 6.4 | 66.2 | 4.5 |
| Example 20 | 10.2 | 83.7 | 3.5 |
| Example 21 | 7.9 | 4.9 | 60.1 |
| Example 22 | 6.5 | 4.0 | 73.4 |
| Example 23 | 7.4 | 5.9 | 49.9 |
| Example 24 | 8.1 | 7.5 | 39.3 |
| Example 25 | 9.1 | 10.3 | 28.6 |
| Example 26 | 10.1 | 12.3 | 24.0 |
| Example 27 | 9.0 | 139.5 | 2.1 |
| Example 28 | 7.4 | 14.8 | 19.9 |
| Example 29 | 6.3 | 13.8 | 21.3 |
| Example 30 | 13.1 | 111.9 | 2.6 |
| Example 31 | 9.9 | 108.1 | 2.7 |
| Example 32 | 9.8 | 15.3 | 19.2 |
| Example 33 | 8.2 | 12.8 | 23.0 |

As shown in Table II, the paclitaxel has markedly higher cytotoxicity against MCF-7/Dx cells in case of treating in combination with the compounds of Examples than when treated alone, and it can be seen that the inventive compounds of formula (I) effectively suppress the activity of p-glycoprotein even at a low concentration of 50 nM.

Test Example 2

In Vivo Absorption of Orally Administered Paclitaxel

In order to investigate the activity of the inventive compounds prepared in Examples, in vivo absorption tests were carried out as follows.

Twenty-five 14- to 15-week-old Sprague-Dawley rats were fasted for over 24 hours while they were allowed free access to water, and then, divided into 4 groups of 5 to 8 rats each Three of the former test groups were orally administered with 20 mg/kg body weight of paclitaxel (6 mg of paclitaxel/0.5 ml of cremophor EL+0.5 ml of ethanol) and each of the compounds of Example 1, 21 and 22 (12 mg of the compounds of Examples/4 ml of 5% dextrose+1.2 mcg of methanesulfonic acid), and the control group was administered with a vehicle (4 ml of 5%-dextrose+1.2 mcg of methanesulfonic acid) and 20 mg of paclitaxel (composition: 6 mg of paclitaxel in 0.5 ml of cremophor EL+0.5 ml of ethanol). Blood samples were taken directly from the heart of each rat before and 1, 2, 4, 6, 8 and 24 hours after the administration.

Each of blood samples was centrifuged at 12,000 rpm to obtain a serum sample, 200 μl of which was mixed with 400 μl of acetonitrile (an internal standard) and the mixture was shaken to obtain an extract. The extract was centrifuged at 12,000 rpm, 4° C. for 5 min to obtain a supernatant. 50 μl of the supernatant was subjected to semi-micro HPLC under the following conditions:
   semi-micro HPLC system: SI-1 model (Shiseido)
   analysis column: Capcell Pak $C_{18}$ UG120 (5 μm, 1.5×250 mm, Shiseido)
   pre-column: Capcell Pak $C_{18}$ MF Ph-1 (4.6×10 mm, Shiseido)

concentration column: Capcell Pak $C_{18}$ UG120 (5 μm, 1.5×35 mm, Shiseido)
mobile phase for pre-column: 20% acetonitrile
mobile phase for analysis column: 55% acetonitrile
injection volume: 5 μl
flow rate: 5 μl/min.
detector: 227 nm The time-dependent changes of the in-blood paclitaxel concentrations are shown in Table III.

TABLE III

|  | AUC (ng · hr/ml)[*1] | Tmax (hr)[*2] | Cmax(ng/ml)[*3] |
|---|---|---|---|
| Control | 440 ± 205 | 2.0 | 78 ± 31 |
| Example 1 | 3,032 ± 1,108 | 1.0 | 1,172 ± 433 |
| Example 21 | 3,744 ± 1,355 | 1.0 | 1,149 ± 529 |
| Example 22 | 3,632 ± 1,219 | 1.0 | 1,120 ± 547 |

[*1]Area under the curve of blood concentration till 24 hours
[*2]Time at the maximum blood concentration
[*3]Maximum blood concentration The results in Table III demonstrate that the inventive compounds can be advantageously used for enhancing the bioavailability of paclitaxel which by itself not readily absorbable in the digestive tract.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I) or a pharmaceutically acceptable salt thereof:

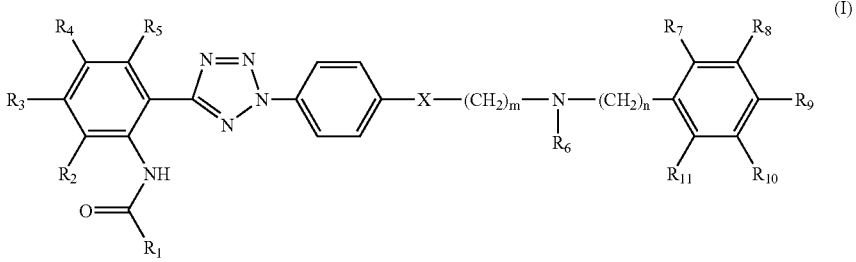

wherein, $R_1$ is aryl, heteroaryl, acrylaryl, acrylheteroaryl, heterocycloalkenyl, or carbocyclo, which is optionally substituted with one or more substituents selected from the group consisting of $C_{1-5}$ alkyl, hydroxy, $C_{1-5}$ alkoxy, halogen, trifluoromethyl, nitro and amino;

$R_2$, $R_3$, $R_4$, $R_5$, $R_6$, $R_7$, $R_8$, $R_9$, $R_{10}$ and $R_{11}$ are each independently hydrogen, hydroxy, halogen, nitro, $C_{1-5}$ alkyl or alkoxy, $R_6$ and $R_{11}$ being optionally fused together to form a 4 to 8-membered ring;

m and n are each independently an integer ranging from 0 to 4; and

X is $CH_2$, O or S.

2. The compound of claim 1, wherein $R_1$ is unsubstituted or substituted phenyl, pyridine, pyrazine, quinoline, isoquinoline, quinazoline, quinoxaline, pyrazole, imidazole, triazole, oxazole, thiazole, oxadiazole, thiadiazole, benzothiazole, benzoxazole, chromone, quinolone, cinnamic or quinoline acryl.

3. The compound of claim 2, which is selected from the group consisting of:

quinoline-3-carboxylic acid [2-(2-4-[2-(6,7-dimethoxy-3,4-dihydro-1H-isoquinolin-2-yl)-ethyl]-phenyl-2H-tetrazol-5-yl)-4,5-dimethoxy-phenyl]-amide;

quinoline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

isoquinoline-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

quinoline-8-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

isoquinoline-1-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

quinoline-4-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

4-methoxy-quinoline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

quinoxaline-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

pyridine-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-nicotinamide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-isonicotinamide;

pyrazine-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-benzamide;

naphthalene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;

N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-2-fluoro-benzamide;
N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-fluoro-benzamide;
N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-4-fluoro-benzamide;
N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3,4-difluoro-benzamide;
thiophene-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
furan-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
6-methyl-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
5-hydroxy-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
5-methoxy-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
6-fluoro-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
6-bromo-4-oxo-4H-chromene-2-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
cinoline-4-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
4-oxo-4H-chromene-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-amide;
quinoline-3-carboxylic acid [2-(2-{4-[2-(6,7-dimethoxy-3,4-dihydro-1H-isoquinolin-2-yl)-ethyl]-phenyl}-2H-tetrazol-5-yl)-4,5-difluoro-phenyl]-amide;
quinoline-3-carboxylic acid [2-(2-{4-[2-(6,7-dimethoxy-3,4-dihydro-1H-isoquinolin-2-yl)-ethylsulfanyl]-phenyl}-2H-tetrazol-5-yl)-4,5-dimethoxy-phenyl]-amide;
N-(2-(2-(4-(2-(6,7-dimethoxy-3,4-dihydroisoquinoline-2(1H)-yl)ethyl)phenyl)-2H-tetrazol-5-yl)-4,5-dimethoxyphenyl)quinoline-3-carboxamide;
N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-phenyl-acrylamide;
N-[2-(2-{4-[2-(6,7-dimethoxy-3,4-dihydro-1H-isoquinolin-2-yl)-ethyl]-phenyl}-2H-tetrazol-5-yl)-4,5-dimethoxy-phenyl]-3-quinolin-3-yl-acrylamide; and
4-oxo-4H-chromene-2-carboxylic acid (2-{2-[4-(2-{[2-(3,4-dimethoxy-phenyl)-ethyl]-methyl-amino}-ethyl)-phenyl]-2H-tetrazol-5-yl}-4,5-dimethoxy-phenyl)-amide.

4. A process for preparing a compound of formula (I), which comprises the steps of:
(i) cyclizing a compound of formula (V) with a compound of formula (VI) in the presence of a base to obtain a compound of formula (IV);
(ii) hydrogenating the compound of formula (IV) in the presence of a catalyst to obtain a compound of formula (II); and
(iii) acylating the compound of formula (II) with a compound of formula (III) in the presence of a base or a condensing agent to give the compound of formula (I):

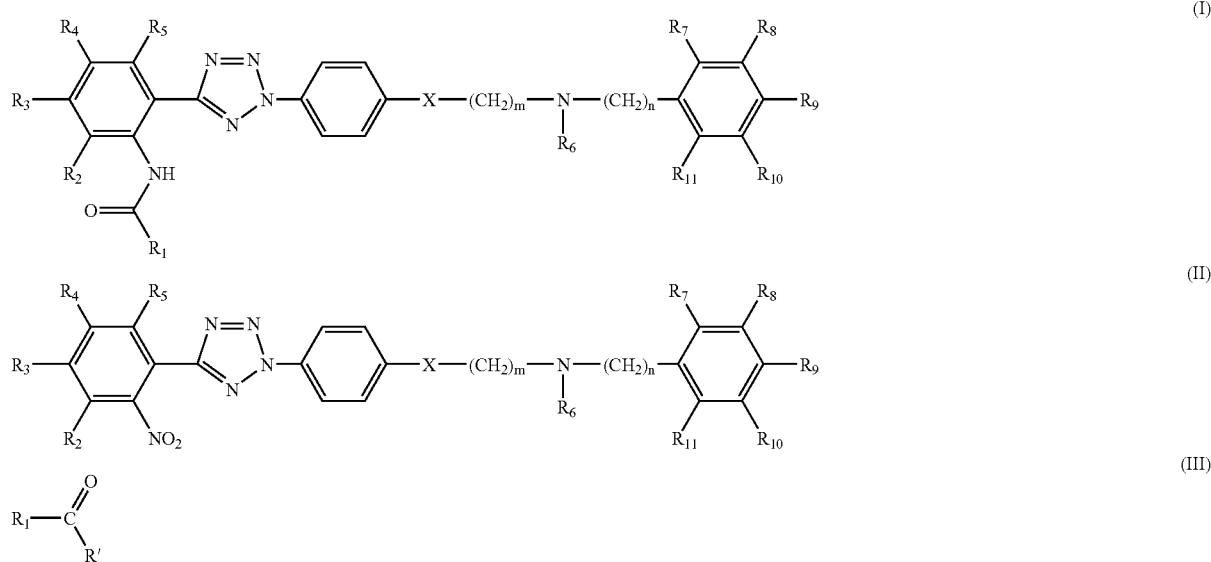

-continued

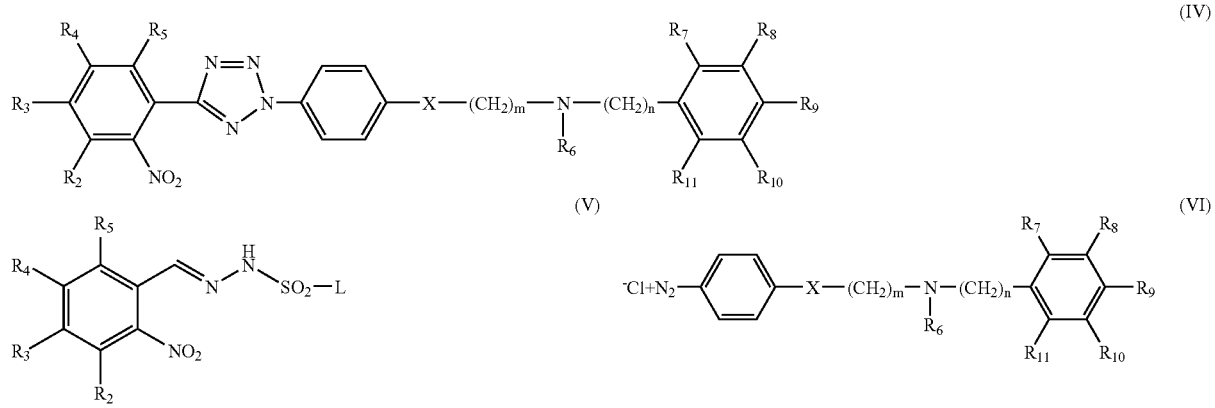

wherein,

R₁ is aryl, heteroaryl, acrylaryl, acrylheteroaryl, heterocycloalkenyl, or carbocyclo, which is optionally substituted with one or more substituents selected from the group consisting of $C_{1-5}$ alkyl, hydroxy, $C_{1-5}$ alkoxy, halogen, trifluoromethyl, nitro and amino;

R₂, R₃, R₄, R₅, R₆, R₇, R₈, R₉, R₁₀ and R₁₁ are each independently hydrogen, hydroxy, halogen, nitro, $C_{1-5}$ alkyl or alkoxy, R₆ and R₁₁ being optionally fused together to form a 4 to 8-membered ring:

m and n are each independently an integer ranging from 0 to 4:

X is CH₂, O or S;

R' is OH, Cl or Br; and

L is benzyl or tolyl.

5. The process of claim 4, wherein the compound of formula (V) is prepared by reacting a compound of formula (VII) with toluenesulfonyl chloride or benzenesulfonyl chloride:

wherein,

R₂, R₃, R₄, R₅ and L have the meanings as defined in claim 4.

6. The process of claim 4, wherein the compound of formula (VI) is prepared by reacting a compound of formula (X) with a compound of formula (XI) in the presence of a base, to obtain a compound of formula (IX); hydrogenating the compound of formula (IX) in the presence of a catalyst, to obtain a compound of formula (VIII); and reacting the compound of formula (VIII) with sodium nitrite and HCl:

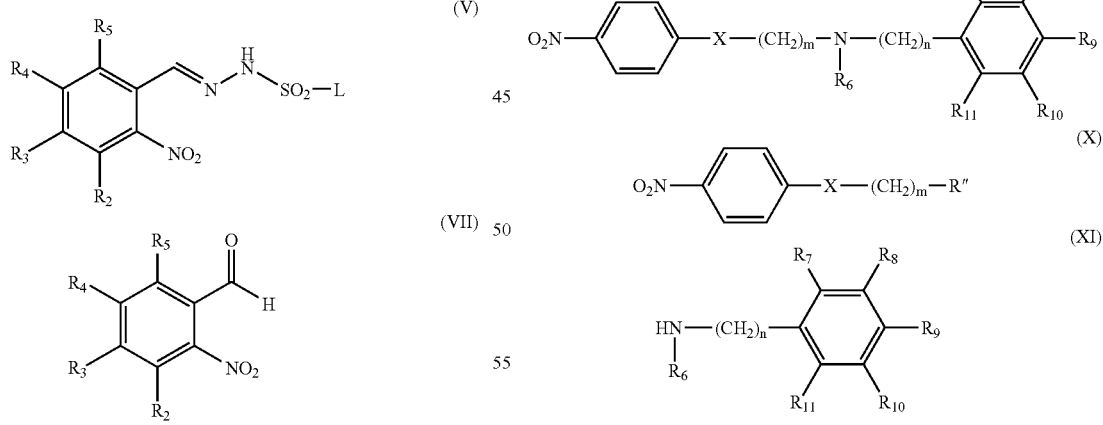

wherein,

R₆, R₇, R₈, R₉, R₁₀, R₁₁, m, n and X have the same meanings as defined in claim 4; and R" is OH, Cl or Br.

7. A pharmaceutical composition for inhibiting the activity of p-glycoprotein comprising a compound of formula (I) or a pharmaceutically acceptable salt thereof as an active ingredient, together with a pharmaceutically acceptable carrier:

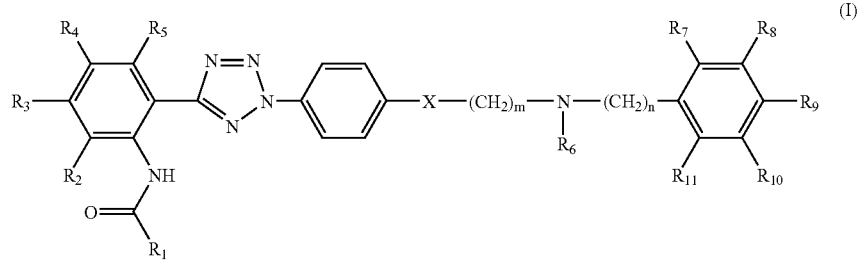

(I)

wherein,

R₁ is aryl, heteroaryl, acrylaryl, acrylheteroaryl, heterocycloalkenyl, or carbocyclo, which is optionally substituted with one or more substituents selected from the group consisting of $C_{1-5}$ alkyl, hydroxy, $C_{1-5}$ alkoxy, halogen, trifluoromethyl, nitro and amino;

$R_2$, $R_3$, $R_4$, $R_5$, $R_6$, $R_7$, $R_8$, $R_9$, $R_{10}$ and $R_{11}$ are each independently hydrogen, hydroxy, halogen, nitro, $C_{1-5}$ alkyl or alkoxy, $R_6$ and $R_{11}$ being optionally fused together to form a 4 to 8-membered ring;

m and n are each independently an integer ranging from 0 to 4; and

X is $CH_2$, O or S.

8. The composition of claim 7, which further comprises an anticancer agent.

9. The composition of claim 8, wherein the anticancer agent is selected from the group consisting of paclitaxel, docetaxel, vincristine, vinblastine, vinorelbin, daunomycin, doxorubicin, topotecan, irinotecan, actinomycin and etopocid.

\* \* \* \* \*